United States Patent
Sang et al.

(10) Patent No.: US 10,822,319 B2
(45) Date of Patent: Nov. 3, 2020

(54) CRYSTAL OF DPP-IV LONG-ACTING INHIBITOR AND SALT

(71) Applicants: CHIA TAI TIANQING PHARMACEUTICAL GROUP CO., LTD., Jiangsu (CN); Lianyungang Runzhong Pharmaceutical Co., Ltd., Lianyungang, Jiangsu (CN); CENTAURUS BIOPHARMA CO., LTD., Beijing (CN)

(72) Inventors: Guangming Sang, Jiangsu (CN); Lin Liu, Jiangsu (CN); Aiming Zhang, Jiangsu (CN); Jiabin Qiao, Jiangsu (CN); Xiaopeng Guo, Jiangsu (CN); Xiquan Zhang, Jiangsu (CN); Chunguang Xia, Jiangsu (CN)

(73) Assignees: CHIA TAI TIANQING PHARMACEUTICAL GROUP CO., LTD., Jiangsu (CN); LIANYUNGANG RUNZHONG PHARMACEUTICAL CO., LTD., Jiangsu (CN); CENTAURUS BIOPHARMA CO., LTD., Beijing (CN)

( * ) Notice: Subject to any disclaimer, the term of this patent is extended or adjusted under 35 U.S.C. 154(b) by 0 days.

(21) Appl. No.: 16/324,884

(22) PCT Filed: Aug. 11, 2017

(86) PCT No.: PCT/CN2017/097046
§ 371 (c)(1),
(2) Date: Feb. 11, 2019

(87) PCT Pub. No.: WO2018/028666
PCT Pub. Date: Feb. 15, 2018

(65) Prior Publication Data
US 2019/0284153 A1      Sep. 19, 2019

(30) Foreign Application Priority Data

Aug. 12, 2016  (CN) .......................... 2016 1 0665625
Aug. 12, 2016  (CN) .......................... 2016 1 0666564

(51) Int. Cl.
| | |
|---|---|
| A61P 3/10 | (2006.01) |
| C07D 405/04 | (2006.01) |
| A61K 31/4035 | (2006.01) |
| C07D 309/14 | (2006.01) |
| A61P 35/00 | (2006.01) |
| A61P 25/00 | (2006.01) |
| A61P 3/12 | (2006.01) |
| A61P 3/00 | (2006.01) |
| A61P 5/50 | (2006.01) |

(52) U.S. Cl.
CPC ........ *C07D 309/14* (2013.01); *A61K 31/4035* (2013.01); *A61P 3/00* (2018.01); *A61P 3/10* (2018.01); *A61P 3/12* (2018.01); *A61P 5/50* (2018.01); *A61P 25/00* (2018.01); *A61P 35/00* (2018.01); *C07D 405/04* (2013.01); *C07B 2200/13* (2013.01)

(58) Field of Classification Search
CPC .......................... C07D 405/04; C07B 2200/13
See application file for complete search history.

(56) References Cited

FOREIGN PATENT DOCUMENTS

| WO | WO 2007097931 | 8/2007 | |
|---|---|---|---|
| WO | WO 2010056708 | 5/2010 | |
| WO | WO-2016127916 A1 * | 8/2016 | ................ A61P 7/00 |
| WO | WO 2017031918 | 3/2017 | |

OTHER PUBLICATIONS

Bhattacharya et al. (Brittain, ed. Polymorphism in Pharmaceutical Solids, 2009, p. 334.*
WO 2017031918A1, published Mar. 2, 2017, Google translation, downloaded Mar. 2, 2020.*
Berge et al. (J. of Pharmaceutical Sciences, 1977, vol. 66(1), pp. 1-19).*
International Search Report and Written Opinion in PCT Appln. No. PCT/CN2017/097046, dated Nov. 15, 2017, 11 Pages, English translation.

* cited by examiner

*Primary Examiner* — Susanna Moore
(74) *Attorney, Agent, or Firm* — Fish & Richardson P.C.

(57) ABSTRACT

The present application relates to a crystal of a compound represented by Formula (I), a salt thereof, and a crystal of the salt thereof, a method for preparing the crystal of the compound represented by Formula (I), the salt thereof, and the crystal of the salt thereof, a crystal comprising the compound represented by Formula (I), a crystal composition comprising the crystal of the salt thereof, a pharmaceutical composition thereof, and medical uses thereof.

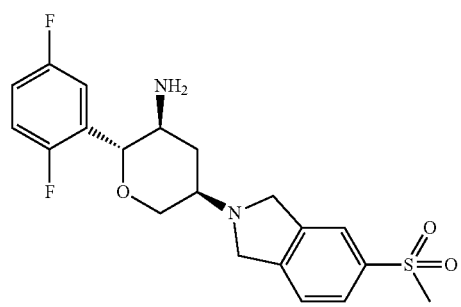

I

18 Claims, 11 Drawing Sheets

CRYSTAL OF DPP-IV LONG-ACTING INHIBITOR AND SALT

CROSS REFERENCE TO RELATED APPLICATION

The present application claims the priorities to and benefits of the Chinese invention patent application Nos. 201610665625.9 and No. 201610666564.8 filed with the China National Intellectual Property Administration on Aug. 12, 2016, both of which are incorporated herein by reference in their entireties.

TECHNICAL FIELD

The present application relates to a crystal of (2R,3S,5R)-5-(5-methanesulfonylisoindolin-2-yl)-2-(2,5-difluorophenyl)tetrahydro-2H-pyran-3-amine as a long-acting inhibitor, a salt thereof, or a crystal of the salt, and a pharmaceutical composition comprising the same and a medical use thereof.

BACKGROUND

Dipeptidyl peptidase-IV (DPP-IV) is a serine protease that can rapidly cleave a protein in which an amino acid at the N-terminus of a peptide chain is proline or alanine, is responsible for a metabolic cleavage of some endogenous peptides (such as GLP-1 and GIP) in vivo, and has shown to have a proteolytic activity against a variety of other peptides (GHRH, NPY, GLP-2 and VIP) in vitro. Because of the degradation of DPP-IV enzyme, GLP- and GIP are rapidly inactivated in vivo, thus inhibiting the activity of DPP-IV would greatly prolong physiological activity duration of GLP-1 and GIP in vivo, which indirectly regulate the insulin secretion and ultimately play a role in controlling a blood glucose level.

As a novel means for treating diabetes, DPP-IV inhibitors can glucose-dependently stimulate insulin secretion, is not prone to have hypoglycemic side effects upon controlling a blood glucose level, and also have some advantages, such as preserving islet β cell function, having few gastrointestinal tract side effects, good tolerance, and the like. DPP-IV inhibitors can be administered orally without the need for injection, and is comparable to existing oral hypoglycemic agents in therapeutic efficacy.

Based on the above features, DPP-IV inhibitors are useful in the treatment and/or prophylaxis of DPP-IV mediated diseases and disorders, such as diabetes, obesity, and the like, particularly type II diabetes.

WO2016127916 discloses substituted amino six-membered saturated heteroalicycles as long-acting DPP-IV inhibitors, including a compound represented by Formula 1 and a process for the preparation thereof, which is incorporated herein by reference in its entirety:

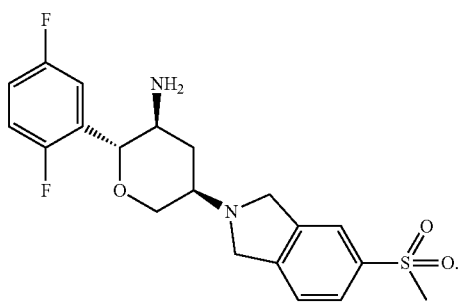

I

SUMMARY OF THE INVENTION

In an aspect, the present application provides a crystal of a compound represented by Formula I, a process for preparing the crystal, a crystalline composition comprising the crystal, a pharmaceutical composition comprising the crystal or the crystalline composition, and a medical use thereof.

In another aspect, the present application provides a phosphate of a compound represented by Formula I, a process for preparing the phosphate, a pharmaceutical composition comprising the phosphate, and a medical use thereof.

In yet another aspect, the present application provides a crystal of a phosphate of a compound represented by Formula I, a process for preparing the crystal of the phosphate, a crystalline composition comprising the crystal of the phosphate, a pharmaceutical composition comprising the crystal of the phosphate or the crystalline composition, and a medical use thereof.

In still another aspect, the application provides a fumarate of a compound represented by Formula I, a process for preparing the fumarate, a pharmaceutical composition comprising the fumarate, and a medical use thereof.

In a further aspect, the present application provides a crystal of a fumarate of a compound represented by Formula I, a process for preparing the crystal of the fumarate, a crystalline composition comprising the crystal of the fumarate, a pharmaceutical composition comprising the crystal of the fumarate or the crystalline composition, and a medical use thereof.

DETAILED DESCRIPTION OF THE INVENTION

In the following description, certain specific details are included to provide a thorough understanding of various disclosed embodiments. However, those skilled in the relevant art will recognize that the embodiments may be practiced without one or more of these specific details, or with other methods, components, materials, and the like.

Unless the context requires otherwise, throughout the specification and claims which follow, the term "comprise" and English variations thereof, such as "comprises" and "comprising", are to be construed in an open and inclusive sense, that is as, "including, but not limited to".

Reference throughout this specification to "one embodiment", or "an embodiment", or "another embodiment", or "some embodiments" means that a particular referent element, structure, or characteristics described in connection with the embodiment is included in at least one embodiment. Accordingly, the appearances of the phase "in one embodiment", or "in an embodiment", or "in another embodiment", or "in some embodiments" in various places throughout this specification are not necessarily all referring to the same embodiment. In addition, the particular elements, structures, or characteristics may be combined in any suitable manner in one or more embodiments.

It should be noted that, as used in this specification and the appended claims, the singular forms "a", "an" and "the" include plural referents unless the content clearly dictates otherwise. Thus, for example, reference to a reaction in which "a catalyst" is involved includes a single catalyst, or two or more catalysts. Unless otherwise explicitly specified herein, it should also be noted that the term "or" is generally employed in its sense including "and/or" unless the content clearly dictates otherwise.

In an aspect, the present application provides a crystal of a compound represented by Formula

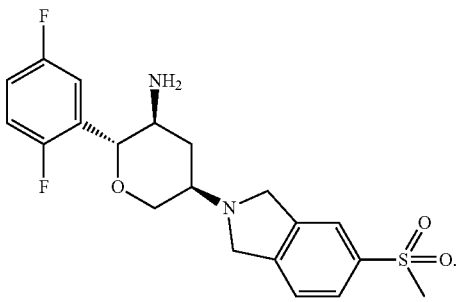

I

In some embodiments of the present application, the crystal of the compound represented by Formula I has diffraction peaks at 2θ=16.4°, 21.8°, 25.3°, and 26.0°±0.2° in an X-ray diffraction (XRD) pattern; typically has diffraction peaks at 2θ=16.4°, 19.4°, 21.2°, 21.8°, 25.3°, and 26.0°±0.2°, and more typically has diffraction peaks at 2θ=13.0°, 16.4°, 18.5°, 19.4°, 21.2°, 21.8°, 25.3°, and 26.0°±0.2°.

In some embodiments of the present application, the X-ray diffraction peaks of the crystal of the compound represented by Formula I have the following characteristics:

| No. | 2θ ± 0.2 (°) | Relative Intensity (%) |
|-----|--------------|------------------------|
| 1   | 12.3         | 3                      |
| 2   | 13.0         | 8                      |
| 3   | 15.0         | 5                      |
| 4   | 16.4         | 18                     |
| 5   | 17.2         | 5                      |
| 6   | 17.6         | 3                      |
| 7   | 18.5         | 9                      |
| 8   | 19.4         | 12                     |
| 9   | 21.2         | 16                     |
| 10  | 21.8         | 100                    |
| 11  | 22.1         | 9                      |
| 12  | 22.5         | 11                     |
| 13  | 22.8         | 5                      |
| 14  | 24.8         | 7                      |
| 15  | 25.3         | 17                     |
| 16  | 26.0         | 39                     |
| 17  | 26.4         | 4                      |
| 18  | 27.5         | 4                      |
| 19  | 27.9         | 6                      |
| 20  | 28.8         | 4                      |
| 21  | 30.4         | 7                      |
| 22  | 30.9         | 4                      |
| 23  | 32.0         | 6                      |
| —   | —            | —                      |

In some embodiments of the present application, the crystal of the compound represented by Formula I has an X-ray diffraction pattern as shown in FIG. 1, 3, 5 or 6. It can be seen from FIGS. 1, 3, 5 and 6 that the crystals of the compound represented by Formula I obtained in different crystallization solvents have substantially the same X-ray diffraction pattern, and therefore they are the same crystalline form.

In some embodiments of the present application, the crystal of the compound represented by Formula I according to the present application can be also characterized by DSC: an onset temperature of 193.3±5° C., and a peak temperature of 195.2±5° C.

In some embodiments of the present application, the crystal of the compound represented by Formula I has a DSC pattern as shown in FIG. 2 or FIG. 4.

The application provides a process for preparing the crystal of the compound represented by Formula I, comprising:

1) dissolving the compound represented by Formula I in a crystallization solvent;
2) cooling for crystallization and then filtering.

In some embodiments of the present application, the crystallization solvent is selected from the group consisting of methanol, ethanol, propanol, isopropanol, n-butanol, isobutanol, tert-butanol, acetone, butanone, ethyl acetate, acetonitrile, dichloromethane, toluene, dioxane, n-heptane, n-hexane, methyl tert-butyl ether, isopropyl ether, isopropyl acetate, and a mixed solvent thereof.

In some embodiments of the present application, the crystallization solvent is selected from the group consisting of methanol, ethanol, propanol, isopropanol, ethyl acetate, acetonitrile, dichloromethane, and a mixed solvent thereof; preferably methanol.

In some embodiments of the present application, the amount of the added crystallization solvent is 2 mL-100 mL, preferably 20 mL, 30 mL, 40 mL, 50 mL, 60 mL, 70 mL, 80 mL, 90 mL, or 100 mL, and more preferably 20 mL-60 mL, 20 mL-40 mL, or 30 mL-50 mL, relative to 1 g of the compound represented by Formula I.

The present application further provides an another process for preparing the crystal of the compound represented by Formula I, comprising precipitating the crystal of the compound represented by Formula I from a solvent comprising methanol.

The present application further provides a crystalline composition comprising the crystal of the compound represented by Formula I. In some embodiments of the present application, the crystal of the compound represented by Formula I accounts for 50 wt % or more, preferably 80 wt % or more, more preferably 90 wt % or more, and most preferably 95 wt % or more by weight of the crystalline composition.

The application further provides a pharmaceutical composition comprising the crystal of the compound represented by Formula I or a crystalline composition comprising the crystal of the compound represented by Formula I. In addition, the pharmaceutical composition may or may not comprise a pharmaceutically acceptable carrier, excipient and/or vehicle.

The present application further provides use of the crystal of the compound represented by Formula I, or a crystalline composition thereof, or a pharmaceutical composition thereof in the preparation of a medicament for the treatment or prevention of a disease benefiting from DPP-IV inhibition. The present application further provides a method for treating or preventing a disease benefiting from DPP-IV inhibition, comprising administering to a subject in need thereof the crystal of the compound represented by Formula I or a crystalline composition thereof or a pharmaceutical composition thereof. The present application further provides the crystal of the compound represented by Formula I, or a crystalline composition thereof, or a pharmaceutical composition thereof for use in the treatment or prevention of a disease benefiting from DPP-IV inhibition. The present application further provides use of the crystal of the compound represented by Formula I, or a crystalline composition thereof, or a pharmaceutical composition thereof in the treatment or prevention of a disease benefiting from DPP-IV inhibition.

In another aspect, the application provides a phosphate of a compound represented by Formula

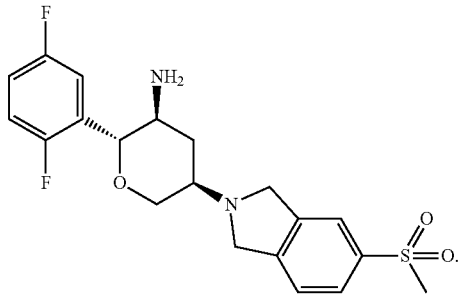

In some embodiments of the present application, a molar ratio of the compound represented by Formula I to phosphoric acid in the phosphate of the compound represented by Formula I is 1:0.5-2, preferably 1:0.5-1, and more preferably 1:1.

In some embodiments of the present application, the phosphate of the compound represented by Formula I is in a crystalline form.

The present application further provides a process for preparing the phosphate of the compound represented by Formula I, comprising contacting the compound represented by Formula I with phosphoric acid and then separating from a solvent. In some embodiments of the present application, the solvent is selected from the group consisting of methanol, ethanol, isopropanol, n-butanol, isobutanol, tert-butanol, dichloromethane, acetonitrile, acetone, ethyl acetate, isopropyl acetate 1,4-dioxane, n-heptane, n-hexane, methyl tert-butyl ether, isopropyl ether, toluene, and a mixture of two or more thereof, preferably ethanol.

In a further aspect, the application provides a crystal of a phosphate of a compound represented by Formula I:

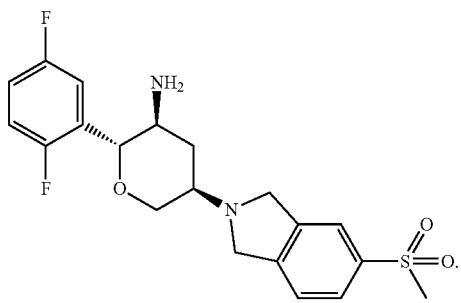

In some embodiments of the present application, the crystal of the phosphate of the compound represented by Formula I has diffraction peaks at 2θ=6.4°, 11.9°, 18.2°, 21.7°, 22.1°, 22.9°, and 23.2°±0.2° in an X-ray diffraction (XRD) pattern; typically has diffraction peaks at 2θ=6.4°, 11.9°, 16.5°, 17.5°, 18.2°, 18.6°, 21.7°, 22.1°, 22.9°, and 23.2°±0.2°, and more typically has diffraction peaks at 2θ=6.4°, 10.1°, 11.9°, 16.5°, 17.5°, 18.2°, 18.6°, 19.8°, 21.7°, 22.1°, 22.9°, 23.2°, and 23.8°±0.2°.

In some embodiments of the present application, the X-ray diffraction peaks of the crystal of the phosphate of the compound represented by Formula I have the following characteristics:

| No. | 2θ ± 0.2 (°) | Relative Intensity (%) |
|---|---|---|
| 1 | 6.4 | 37 |
| 2 | 10.1 | 14 |
| 3 | 11.9 | 39 |
| 4 | 16.5 | 38 |
| 5 | 17.5 | 38 |
| 6 | 18.2 | 70 |
| 7 | 18.6 | 40 |
| 8 | 19.8 | 32 |
| 9 | 21.7 | 100 |
| 10 | 22.1 | 66 |
| 11 | 22.9 | 55 |
| 12 | 23.2 | 56 |
| 13 | 23.8 | 41 |
| 14 | 24.0 | 38 |
| 15 | 31.2 | 35 |
| — | — | — |

In some embodiments of the present application, the crystal of the phosphate of the compound represented by Formula I has an X-ray diffraction pattern as shown in FIG. 7.

In some embodiments of the present application, the crystal of the phosphate of the compound represented by Formula I has a DSC pattern as shown in FIG. 8.

The present application further provides a process for preparing the crystal of the phosphate of the compound represented by Formula I, comprising contacting the compound represented by Formula I with phosphoric acid and then crystallizing from a solvent. In some embodiments of the present application, the solvent is selected from the group consisting of methanol, ethanol, isopropanol, n-butanol, isobutanol, tert-butanol, dichloromethane, acetonitrile, acetone, ethyl acetate, isopropyl acetate 1,4-dioxane, n-heptane, n-hexane, methyl tert-butyl ether, isopropyl ether, toluene and a mixture of two or more thereof, preferably ethanol.

The present application further provides a crystalline composition comprising the crystal of the phosphate of the compound represented by Formula I. In some embodiments of the present application, the crystal of the phosphate of the compound represented by Formula I accounts for 50 wt % or more, preferably 80 wt % or more, more preferably 90 wt % or more, and most preferably 95 wt % or more by weight of the crystalline composition.

The application further provides a pharmaceutical composition comprising the phosphate of the compound represented by Formula I, or the crystal of the phosphate of the compound represented by Formula I, or a crystalline composition comprising the crystal of the phosphate of the compound represented by Formula I. In some embodiments of the present application, the pharmaceutical composition comprises a therapeutically effective amount of the phosphate of the compound represented by Formula I, or the crystal of the phosphate of the compound represented by Formula I. In addition, the pharmaceutical composition may or may not comprise a pharmaceutically acceptable carrier, excipient and/or vehicle.

The present application further provides use of the phosphate of the compound represented by Formula I, or the crystal of the phosphate of the compound represented by Formula I or a crystalline composition thereof, or a pharmaceutical composition thereof in the preparation of a medicament for the treatment or prevention of a disease benefiting from DPP-IV inhibition. The present application further provides a method for treating or preventing a disease benefiting from DPP-IV inhibition, comprising administering to a subject in need thereof the phosphate of the compound represented by Formula I, or the crystal of the phosphate of the compound represented by Formula I or a crystalline composition thereof, or a pharmaceutical composition thereof. The present application further provides the phosphate of the compound represented by Formula I, or the crystal of the phosphate of the compound represented by Formula I or a crystalline composition thereof, or a pharmaceutical composition thereof for use in the treatment or prevention of a disease benefiting from DPP-IV inhibition. The present application further provides use of the phosphate of the compound represented by Formula I, or the crystal of the phosphate of the compound represented by Formula I or a crystalline composition thereof, or a pharmaceutical composition thereof in the treatment or prevention of a disease benefiting from DPP-IV inhibition.

In another aspect, the application provides a fumarate of a compound represented by Formula I:

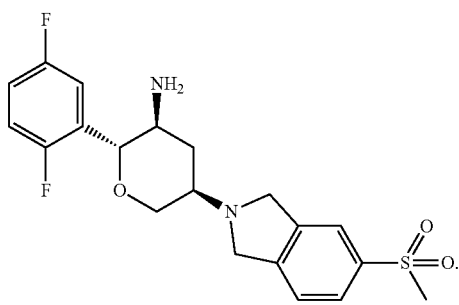

In some embodiments of the present application, a molar ratio of the compound represented by Formula I to fumaric acid in the fumarate of the compound represented by Formula I is 1:0.5-2, preferably 1:0.5-1, and more preferably 1:0.5.

In some embodiments of the present application, the fumarate of the compound represented by Formula I may be in a crystalline form.

The present application further provides a process for preparing the fumarate of the compound represented by Formula I, comprising contacting the compound represented by Formula I with fumaric acid and then separating from a solvent. In some embodiments of the present application, the solvent is selected from the group consisting of methanol, ethanol, isopropanol, n-butanol, isobutanol, tert-butanol, dichloromethane, acetonitrile, acetone, ethyl acetate, isopropyl acetate 1,4-dioxane, n-heptane, n-hexane, methyl tert-butyl ether, isopropyl ether, toluene, and a mixture of two or more thereof, preferably ethanol.

In a further aspect, the application provides a crystal of a fumarate of a compound represented by Formula I:

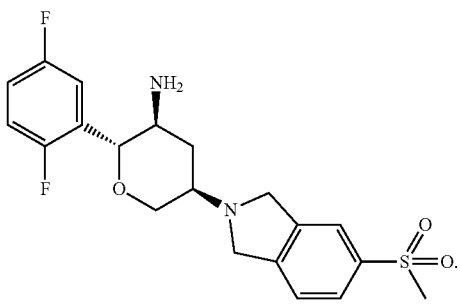

In some embodiments of the present application, the crystal of the fumarate of the compound represented by Formula I has a diffraction peak at 2θ=20.67°±0.2° in an X-ray diffraction (XRD) pattern. In some embodiments of the present application, the crystal of the fumarate of the compound represented by Formula I has an X-ray diffraction pattern as shown in FIG. 9.

In some embodiments of the present application, the crystal of the fumarate of the compound represented by Formula I has a DSC pattern as shown in FIG. 10.

The present application further provides a process for preparing the crystal of the fumarate of the compound represented by Formula I, comprising contacting the compound represented by Formula I with fumaric acid and then crystallizing from a solvent. In some embodiments of the present application, the solvent is selected from the group consisting of methanol, ethanol, isopropanol, n-butanol, isobutanol, tert-butanol, dichloromethane, acetonitrile, acetone, ethyl acetate, isopropyl acetate 1,4-dioxane, n-heptane, n-hexane, methyl tert-butyl ether, isopropyl ether, toluene and a mixture of two or more thereof, preferably ethanol.

The present application further provides a crystalline composition comprising the crystal of the fumarate of the compound represented by Formula I. In some embodiments of the present application, the crystal of the fumarate of the compound represented by Formula I accounts for 50 wt % or more, preferably 80 wt % or more, more preferably 90 wt % or more, and most preferably 95 wt % or more by weight of the crystalline composition.

The application further provides a pharmaceutical composition comprising the fumarate of the compound represented by Formula I, or the crystal of the fumarate of the compound represented by Formula I, or a crystalline composition comprising the crystal of the fumarate of the compound represented by Formula I. In some embodiments of the present application, the pharmaceutical composition comprises a therapeutically effective amount of the fumarate of the compound represented by Formula I, or the crystal of the fumarate of the compound represented by Formula I.

In addition, the pharmaceutical composition may or may not comprise a pharmaceutically acceptable carrier, excipient and/or vehicle.

The present application further provides use of the fumarate of the compound represented by Formula I, or the crystal of the fumarate of the compound represented by Formula I or a crystalline composition thereof, or a pharmaceutical composition thereof in the preparation of a medicament for the treatment or prevention of a disease benefiting from DPP-IV inhibition. The present application further provides a method for treating or preventing a disease benefiting from DPP-IV inhibition, comprising administering to a subject in need thereof the fumarate of the compound represented by Formula I, or the crystal of the fumarate of the compound represented by Formula I or a crystalline composition thereof, or a pharmaceutical composition thereof. The present application further provides the fumarate of the compound represented by Formula I, or the crystal of the fumarate of the compound represented by Formula I or a crystalline composition thereof, or a pharmaceutical composition thereof for use in the treatment or prevention of a disease benefiting from DPP-IV inhibition. The present application further provides use of the fumarate of the compound represented by Formula I, or the crystal of the fumarate of the compound represented by Formula I or a crystalline composition thereof, or a pharmaceutical composition thereof in the treatment or prevention of a disease benefiting from DPP-IV inhibition.

In some embodiments of the present application, the disease benefiting from DPP-IV inhibition is selected from the group consisting of insulin resistance, hyperglycemia, type II diabetes, diabetic dyslipidemia, impaired glucose tolerance (IGT), impaired fasting glucose (IFG), metabolic acidosis, ketosis, appetite regulation, obesity, various cancers, neurological disorders, immune system disorders, and the like, preferably type II diabetes or obesity.

In the present application. X-ray diffraction spectrums are measured by the following method: instrument: Bruker D8 ADVANCE X-ray diffractometer; method: target: Cu: K-Alpha: wavelength $\lambda=1.54179$ Å; tube voltage: 40 kV: tube current: 40 mA: scan range: 4-40° C.; sample rotation speed: 15 rpm; scanning speed: 10°/min. Alternatively, they can be also measured by the following method: instrument: Bruker D8 ADVANCE X-ray diffractometer; method: target: Cu; wavelength $\lambda=1.5418$ Å: tube voltage: 40 kV; tube current: 40 mA; scan range: 3-40° C.; scanning speed: 0.1 sec/step, and 0.02° C./step.

In the present application, differential scanning calorimetry (DSC) is measured by the following method: instrument: TA Q2000 differential scanning calorimeter; method: a sample (~1 mg) is placed in a DSC aluminum pan and measured at a temperature of 25° C. to 300° C. at a heating rate of 10° C./min.

A ratio of the compound represented by Formula I to the corresponding acid in the phosphate or fumarate of the compound represented by Formula I according to the present application can be measured by a titration method. Titrator: METTLER T50; titration solution: 0.1 mol/L sodium hydroxide titration solution: titration solvent: water.

It should be noticed that in an X-ray diffraction spectrum, a diffraction pattern of a crystalline compound is frequently characteristic for a specific crystalline form. Relative intensities of the bands (especially at the low angle) can vary depending upon preferential orientation effects resulting from the crystallization conditions, particle size, and different measuring conditions. Therefore, relative intensities of diffraction peaks are not characteristic for a specific crystalline form. It is the relative position of peaks rather than relative intensities thereof that should be paid more attention when judging whether a crystalline form is the same as the known crystalline form. In addition, as for any given crystalline form, there may be a slight error in the position of a peak, which is also well known in the field of crystallography. For example, the position of a peak may shift due to the change of a temperature, the movement of a sample or the calibration of an instrument and so on when analyzing the sample, and the measurement error of $2\theta$ value sometimes is about ±0.2°. Accordingly, this error should be taken into consideration when identifying the structure of a crystalline form. Usually, the position of a peak is expressed in terms of $2\theta$ angle or lattice spacing d in XRD spectrum and the simple conversion relationship therebetween is $d=\lambda/2 \sin \theta$, wherein d represents the lattice spacing, h represents the wavelength of incident X-ray, and $\theta$ represents the diffraction angle. For the same crystalline form of the same compound, the position of a peak in XRD spectrum thereof has similarity on the whole, and accordingly the error of a relative intensity may be relatively large. In addition, it is necessary to point out that due to some factors such as reduced contents, parts of diffraction lines may be absent in identification of a mixture. At this time, even a band may be characteristic for the given crystal without depending upon the whole bands of a high purity sample.

It should be noted that DSC is used to measure a thermal transition temperature of a crystal when absorbing or releasing heat due to the structural change of the crystal or the melting of the crystal. In a continuous analysis of the same crystalline form of the same compound, the error of a thermal transition temperature and a melting point is typically within a range of about ±5° C. A compound with a given DSC peak or melting point means that the DSC peak or melting point may be varied within a range of ±5° C. DSC provides an auxiliary method to distinguish different crystalline forms. Different crystalline forms can be identified by their characteristically different transition temperatures.

In the present application, the term "pharmaceutical composition" refers to a formulation which comprises an active compound of the present application and a carrier, excipient and/or vehicle that is generally accepted in the art for the delivery of a biologically active compound to an organism (e.g., a human). The purpose of pharmaceutical composition is to facilitate the administration of the compound of the present application to the organism.

In the present application, the term "pharmaceutically acceptable carrier" refers to a carrier and diluent which do not cause significant stimulation to an organism (e.g., a human), and will not impair the bioactivity and properties of an active compound. "Pharmaceutically acceptable excipient and/or vehicle" refers to an inert substance which is administered together with an active ingredient and is beneficial to the administration of an active ingredient. "Pharmaceutically acceptable carrier, excipient, and/or vehicle" includes, but is not limited to, any carriers, excipients, vehicles, glidants, sweetening agents, diluents, preservatives, dyes/colorants, flavoring agents, surfactants, wetting agents, dispersants, disintegrants, suspending agents, stabilizers, isotonic agents, solvents and emulsifiers, and the like, which are acceptable for use in humans or animals (such as livestock). Non-limiting examples of an excipient include calcium carbonate, calcium phosphate, various sugars and starches, cellulose derivatives, gelatine, vegetable oils and polyethylene glycols, and the like.

The compound of the present application or its salts, or crystals thereof, or crystalline compositions thereof may be administered in their pure forms or in the form of suitable pharmaceutical compositions through any acceptable administration routes of a medicament providing a similar use. The pharmaceutical compositions of the present application may be prepared by combining the compound of the present application or its salts, or crystals thereof, or crystalline compositions thereof with a suitable pharmaceutically acceptable carrier, diluent, vehicle or excipient. The pharmaceutical compositions of the present application may be formulated into solid, semi-solid, liquid or gaseous formulations, such as tablets, pills, capsules, powders, granules, ointments, emulsions, suspensions, solutions, suppositories, injections, inhalants, gels, microspheres, aerosols, and the like.

Typical administration routes of the compound of the present application or its salts, or crystals thereof, or crystalline compositions thereof, or pharmaceutical compositions thereof include, but are not limited to, oral, rectal, transmucosal, enteral administration, or local, transdermal, inhalation, parenteral, sublingual, intravaginal, intranasal, intraocular, intraperitoneal, intramuscular, subcutaneous, intravenous administration and the like. The preferred administration route is the oral administration.

The pharmaceutical compositions of the present application can be prepared by using methods well-known to those of ordinary skill in the art, such as conventional mixing method, dissolution method, granulation method, dragee preparation method, grinding method, emulsification method, freeze-drying method, and the like.

In preferred embodiments, the pharmaceutical compositions are in oral form. For oral administration, the pharmaceutical compositions may be formulated by mixing an active compound with a pharmaceutically acceptable carrier, excipient, and/or vehicle well-known in the art. Such a carrier, excipient, and vehicle enable the compound of the present application or its salts, or crystals thereof, or crystalline compositions thereof to be formulated into tablets, pills, lozenges, dragees, capsules, liquids, gels, syrups, suspensions, and the like, for oral administration to patients.

A solid oral pharmaceutical composition can be prepared by a conventional mixing, filling or tabletting method. For example, it can be obtained by mixing the active compound with a solid excipient, optionally grinding the resulting mixture, adding other suitable excipients, if necessary, and then processing the mixture into granules to obtain tablets or cores of dragees. Suitable excipients include, but are not limited to, fillers, such as sugars, including lactose, sucrose, mannitol or sorbitol; celluloses, such as microcrystalline cellulose, corn starch, wheat starch, rice starch and potato starch; and other substances, such as pectin, gelatin, tragacanth, methylcellulose, hydroxypropylmethylcellulose, sodium carboxymethylcellulose and/or polyvinylpyrrolidone; disintegrants, such as sodium carboxymethyl starch, crosslinked sodium carboxymethylcellulose, crosslinked polyvinylpyrrolidone, agar or alginic acid, and a salt such as sodium alginate can be also used. The cores of dragees may be optionally coated according to well-known methods in the pharmaceutical practice, in particular using an enteric coating.

All the solvents used in the present application are commercially available, and can be used without a further purification. A reaction is generally carried out under an inert atmosphere such as a nitrogen atmosphere and in an anhydrous solvent.

The crystal of the compound represented by Formula I provided in the present application has one or more advantages, such as high purity, high crystallinity, good stability and so on. Moreover, the process for preparing the crystal of the compound represented by the Formula I provided in the present application has one or more advantages, such as simplified operation, inexpensive and readily available solvent, mild crystallization conditions, and so on, and is suitable for industrial production. The process for preparing the salts of the compound represented by Formula I provided in the present application is simple to operate, and the resulting salts of the compound represented by Formula I have a high purity and good pharmacokinetic properties, and are suitable for being prepared as a desired pharmaceutical composition.

EXAMPLES

Figure 1:
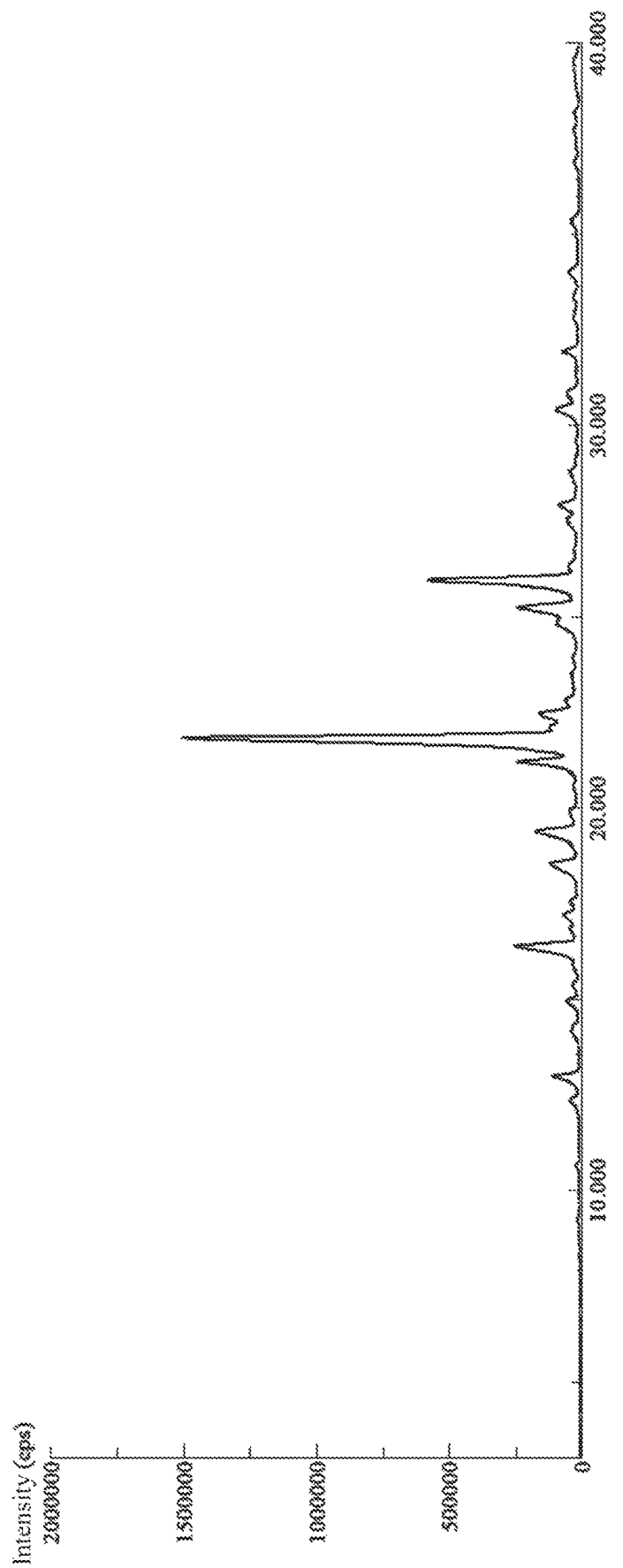
FIG. 1 shows an XRD pattern of the crystal of the compound represented by Formula I.

The disclosure of the present application is illustrated below with reference to specific examples, but these specific examples do not limit the scope of the present application.

Example 1: 5-Methanesulfonylisoindoline Hydrochloride (2)

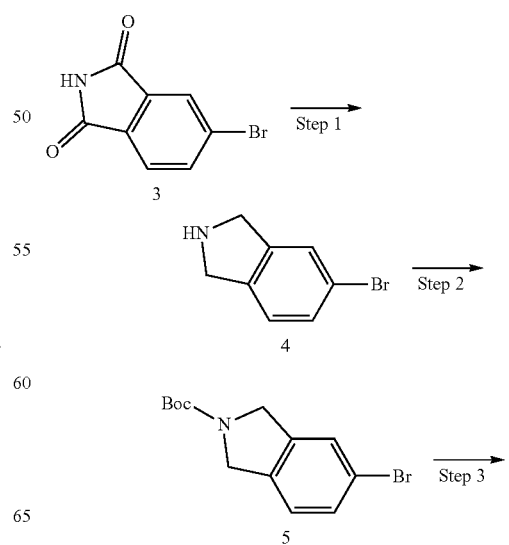

-continued

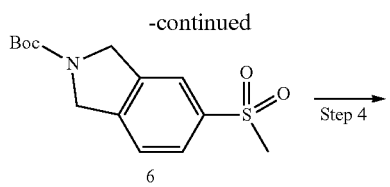

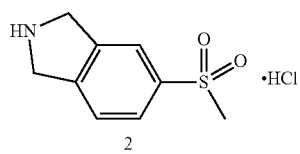

Step 1: 5-bromoisoindoline (4)

To a compound represented by Formula 3 (22.6 g, 100 mmol) in dried tetrahydrofuran (250 mL) was added dropwise borane-dimethyl sulfide complex (51 mL, 500 mmol), stirred for 2 hours at room temperature, and then refluxed overnight. After cooling, methanol was carefully added dropwise to quench the excess borane. The resulting mixture was evaporated and concentrated, and then the residue was purified by silica gel column chromatography to afford 5-bromoisoindoline (10.36 g). Yield: 52%. MS m/z [ESI]: 198.0[M+1].

Step 2: 5-bromo-2-tert-butoxycarbonylisoindoline (5)
The compound represented by Formula 4 (10.36 g, 52.3 mmol) was dissolved in 80 mL dichloromethane, and cooled in an ice bath. Boc anhydride (22.8 g, 104.6 mmol) was added dropwise followed by the addition of sodium carbonate (16.6 g, 156.9 mmol) and water (150 mL), and stirred for 4 hours in an ice bath. The organic phase was separated, washed with brine, and concentrated, and then the residue was purified by silica gel column chromatography to afford the product 5-bromo-2-tert-butoxycarbonylisoindoline (13.3 g). Yield: 85%. MS m/z [ESI]: 298.0[M+1]. $^1$H-NMR (400 MHz, CDCl$_3$): δ=7.37 (2H, m), 7.11 (1H, m), 4.62 (4H, m), 1.51 (9H, s).

Step 3: 5-methanesulfonyl-2-tert-butoxycarbonylisoindoline (6)

The compound represented by Formula 5 (5.96 g, 20 mmol), sodium methylsulfinate (90%, 2.94 g, 26 mmol), cuprous iodide (762 mg, 4 mmol) and L-proline (920 mg, 8 mmol) were added to dimethylsulfoxide (80 mL), purged with nitrogen to remove air, and stirred for 2 days at 120° C. After cooling, the resulting mixture was poured into water and extracted with ethyl acetate. The organic phase was dried, evaporated, and concentrated, and then the residue was purified by silica gel column chromatography to afford 5-methanesulfonyl-2-tert-butoxycarbonylisoindoline (5.46 g). Yield: 92%. MS m/z [ESI]: 298.1 [M+1].

Step 4: 5-Methanesulfonylisoindoline Hydrochloride (2)

A solution of the compound represented by Formula 6 (5.46 g, 18.4 mmol) in methanol/dichloromethane (1:1, 80 mL) was purged with hydrogen chloride gas until saturation, and stirred for 1 hour at room temperature. After the reaction mixture was poured into 800 mL ethyl ether, the precipitate was collected by filtration, washed with ethyl ether and dried to afford the product 5-methanesulfonylisoindoline hydrochloride (3.44 g). Yield: 80%. MS m/z [ESI]: 198.0 [M+1]. $^1$H-NMR (400 MHz, CDCl$_3$): b=7.82 (1H, s), 7.81 (1H, d, J=8.0 Hz), 7.43 (1H, d, J=8.0 Hz), 4.31 (4H, s), 3.05 (3H, s), 2.30 (2H, brs).

Example 2: (2R,3S,5R)-5-(5-methanesulfonylisoindolin-2-yl)-2-(2,5-difluorophenyl) tetrahydro-2H-pyran-3-amine Crude Product Step 1: tert-butyl (2R,3S,5R)-5-(5-methanesulfonylisoindolin-2-yl)-2-(2,5-difluorophenyl) tetrahydro-2H-pyran-3-ylcarbamate (8)

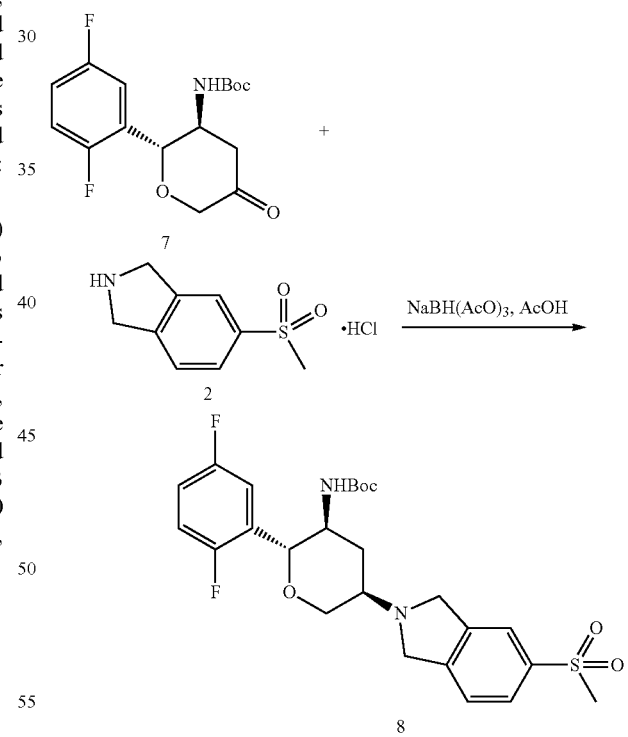

To 2.25 L of N,N-diisopropylacetamide solvent were added a compound represented by Formula 7 (150 g, 458.27 mmol) and the compound represented by Formula 2 (117.82 g, 504.09 mmol), stirred uniformly and cooled to −10° C., and then to the reaction system was slowly added dropwise acetic acid (26.26 mL, 458.27 mmol). After the addition was completed. NaBH(AcO)$_3$ (194.25 g, 916.54 mmol) was added, and then the resulting mixture was to reacted for 1 h under stirring while maintaining this temperature. The temperature was controlled below 20° C., and the reaction system was adjusted to pH=10 with an aqueous ammonia solution, stirred for 15 min, and then filtered under suction. The filter cake was slurried and washed with purified water, and then filtered under suction. The resulting filter cake was forced air-dried at 60° C. to afford 223.5 g of the compound represented by Formula 8. Yield: 95%.

Step 2: (2R,3S,5R)-5-(5-methanesulfonylisoindolin-2-yl)-2-(2,5-difluorophenyl)tetrahydro-2H-pyran-3-amine (I) Crude Product

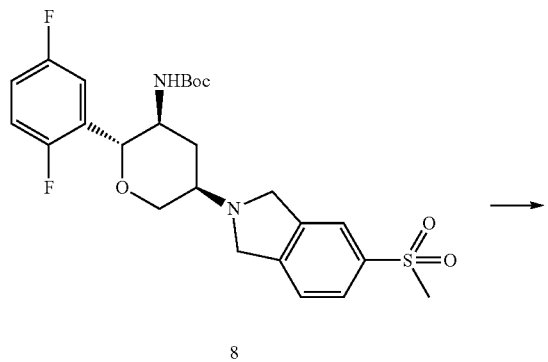

8

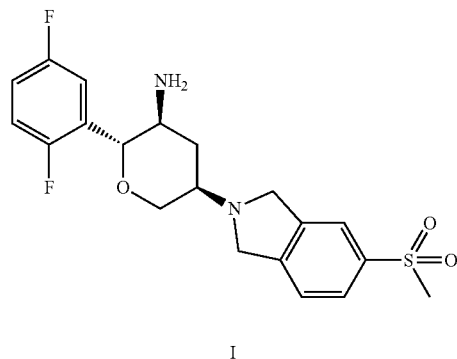

I

To 0.2 L of a mixed solvent of N,N-diisopropylacetamide and purified water (v/v=1/1) was added the compound represented by Formula 8 (202 g, 396.44 mmol), and stirred uniformly, and to the resulting mixture was slowly added dropwise a sulfuric acid solution (1.1 L, 5.95 mol). After the addition was completed, the reaction system was heated to 40° C. and reacted for 2 h under stirring. Then, the resulting solution was adjusted to about pH=10 by adding dropwise an aqueous ammonia solution. After the dropwise addition was completed, the resulting mixture was stirred for 1 h. and then filtered under suction. The filter cake was washed with purified water, and then forced air-dried at 60° C. to afford 133.1 g of the compound represented by Formula I as a crude product. Yield: 83%.

Example 3: A Crystal of (2R,3S,5R)-5-(5-methanesulfonylisoindolin-2-yl)-2-(2,5-difluorophenyl)tetrahydro-2H-pyran-3-amine (I)

Method I 130 g of the crude product was added to 650 mL of anhydrous methanol, heated and dissolved to obtain a clear solution. The solution was then decolorized with activated carbon, and hot-filtered under suction. The filtrate was cooled to room temperature, crystallized for 2 h, and then filtered under suction. The filter cake was forced air-dried at 60° C. to afford 94.2 g of the crystal. Yield: 72.4%.

Method II

Anhydrous methanol (26.8 L) was heated to reflux, and then the crude product (670 g) was added thereto, dissolved, and filtered. The filtrate was cooled to ~5° C. to 5° C., crystallized for 1 h and then filtered under suction. The filter cake was rinsed with anhydrous methanol, and forced air-dried at 50° C.–60° C. for 10-12 h to afford 528 g of the crystal. Yield: 78%.

Figure 2:
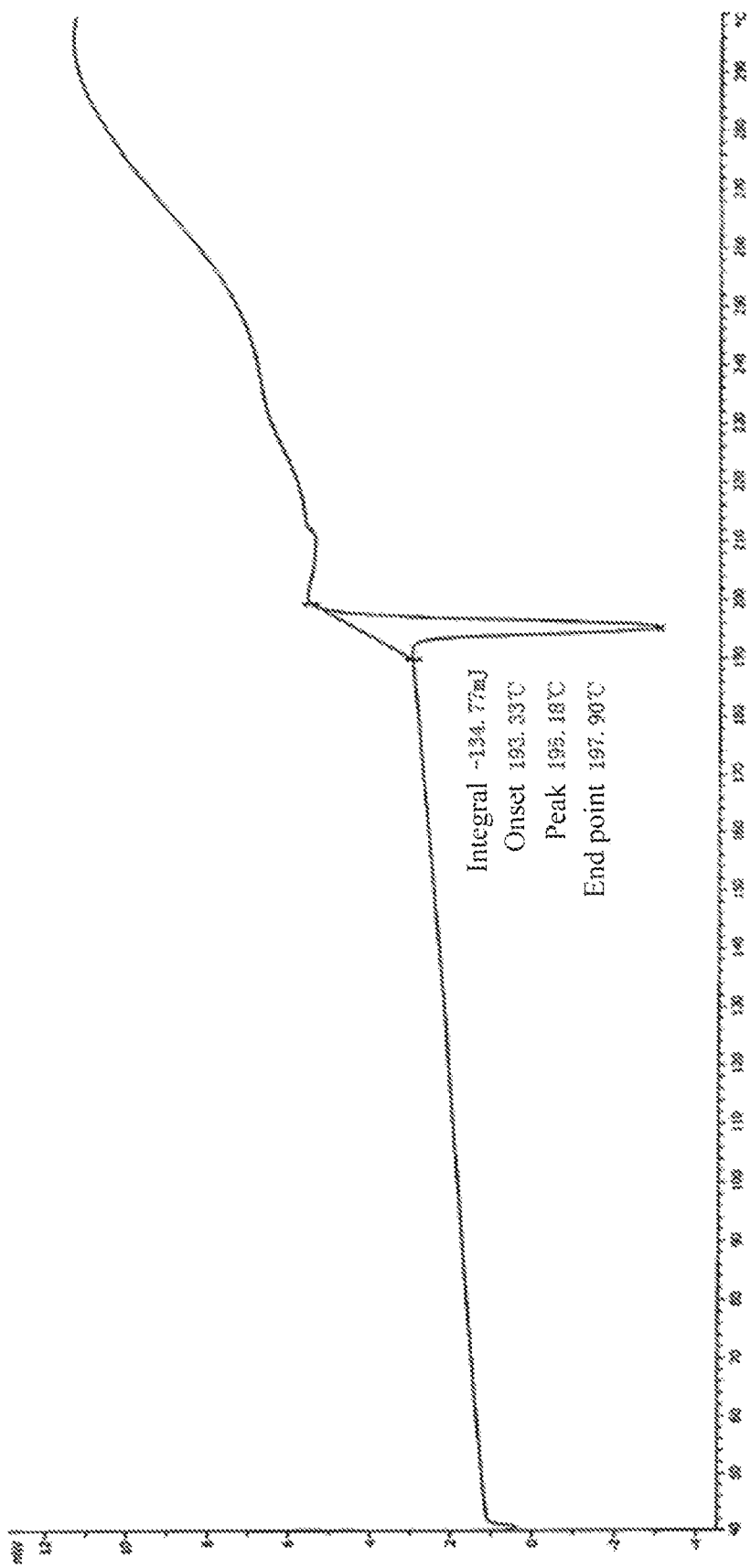
FIG. 2 shows a DSC pattern of the crystal of the compound represented by Formula I.

A typical XRD pattern of the crystal prepared by the method I using methanol as the crystallization solvent was shown in FIG. 1 and the DSC pattern was shown in FIG. 2.

Figure 3:
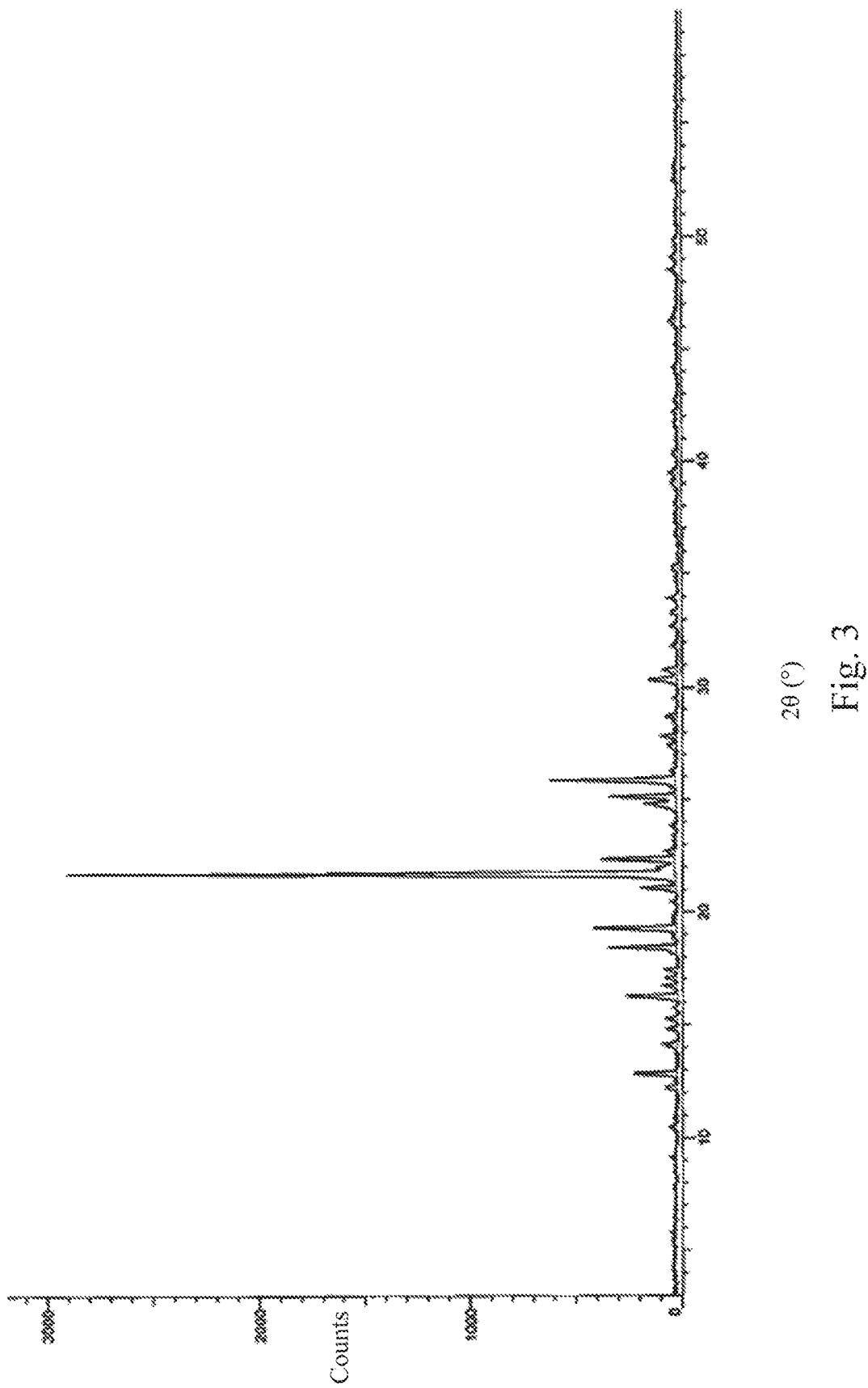
FIG. 3 shows an XRD pattern of the crystal of the compound represented by Formula I.
Figure 4:
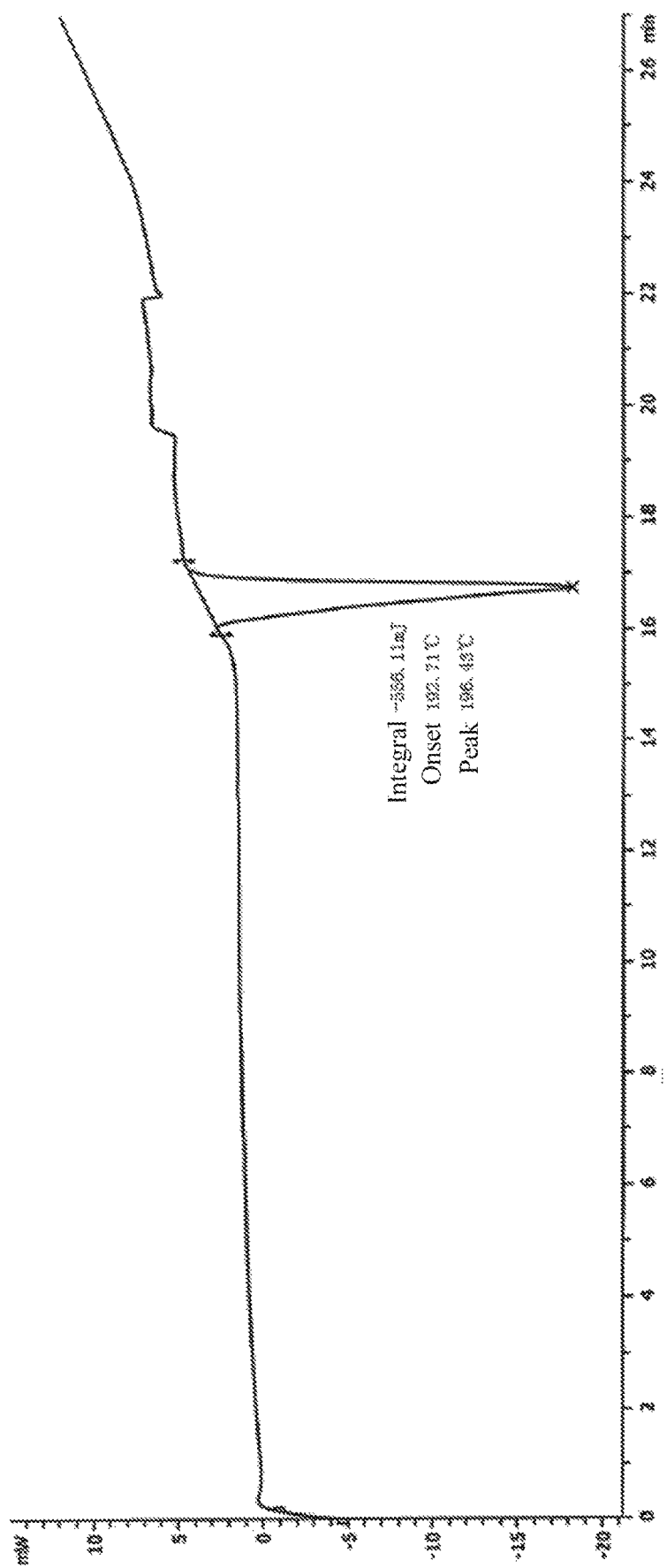
FIG. 4 shows a DSC pattern of the crystal of the compound represented by Formula I.

Another typical XRD pattern of the crystal prepared by the method II using methanol as the crystallization solvent was shown in FIG. 3 and the DSC pattern was shown in FIG. 4.

with reference to the procedure similar to that of Method I or Method II in Example 3, the crystallization solvent was replaced, and the resulting crystals were shown in the table below.

Figure 5:
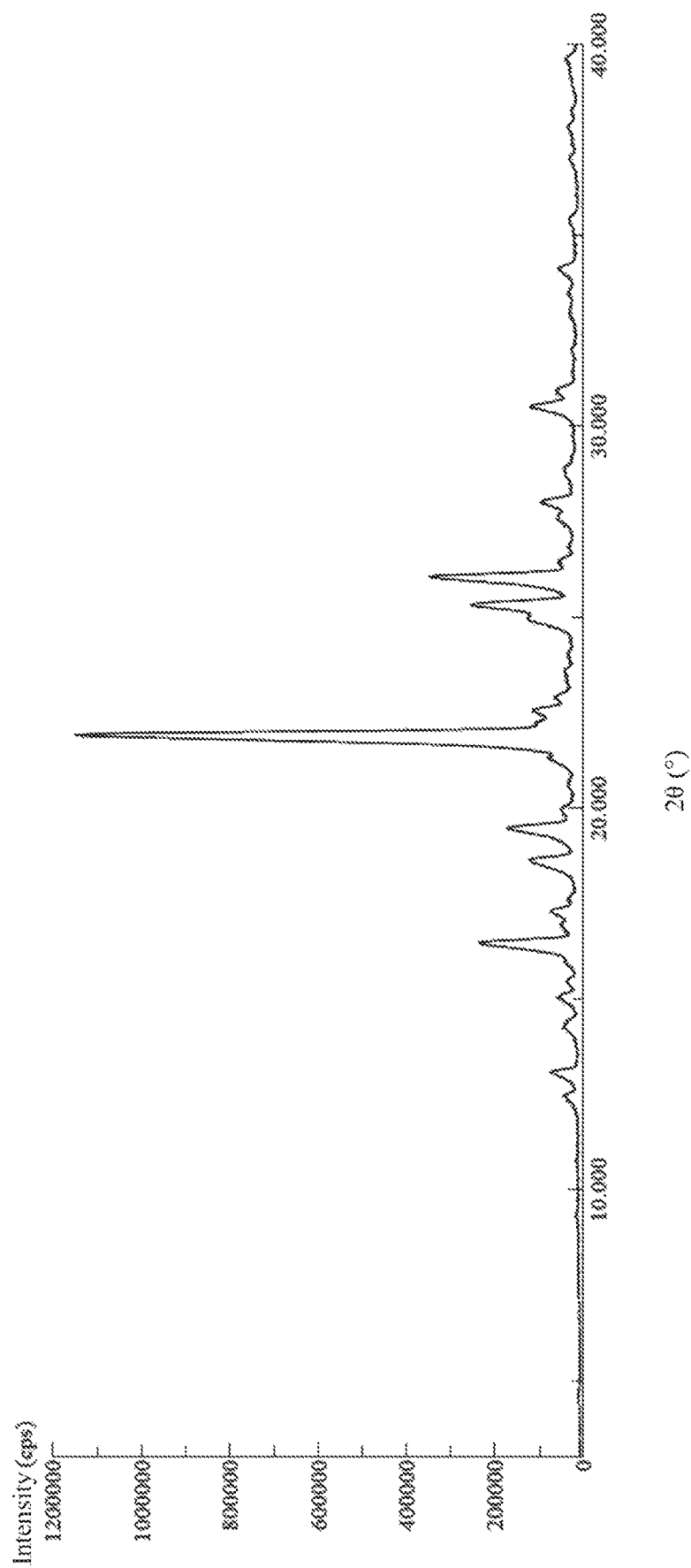
FIG. 5 shows an XRD pattern of the crystal of the compound represented by Formula I.
Figure 6:
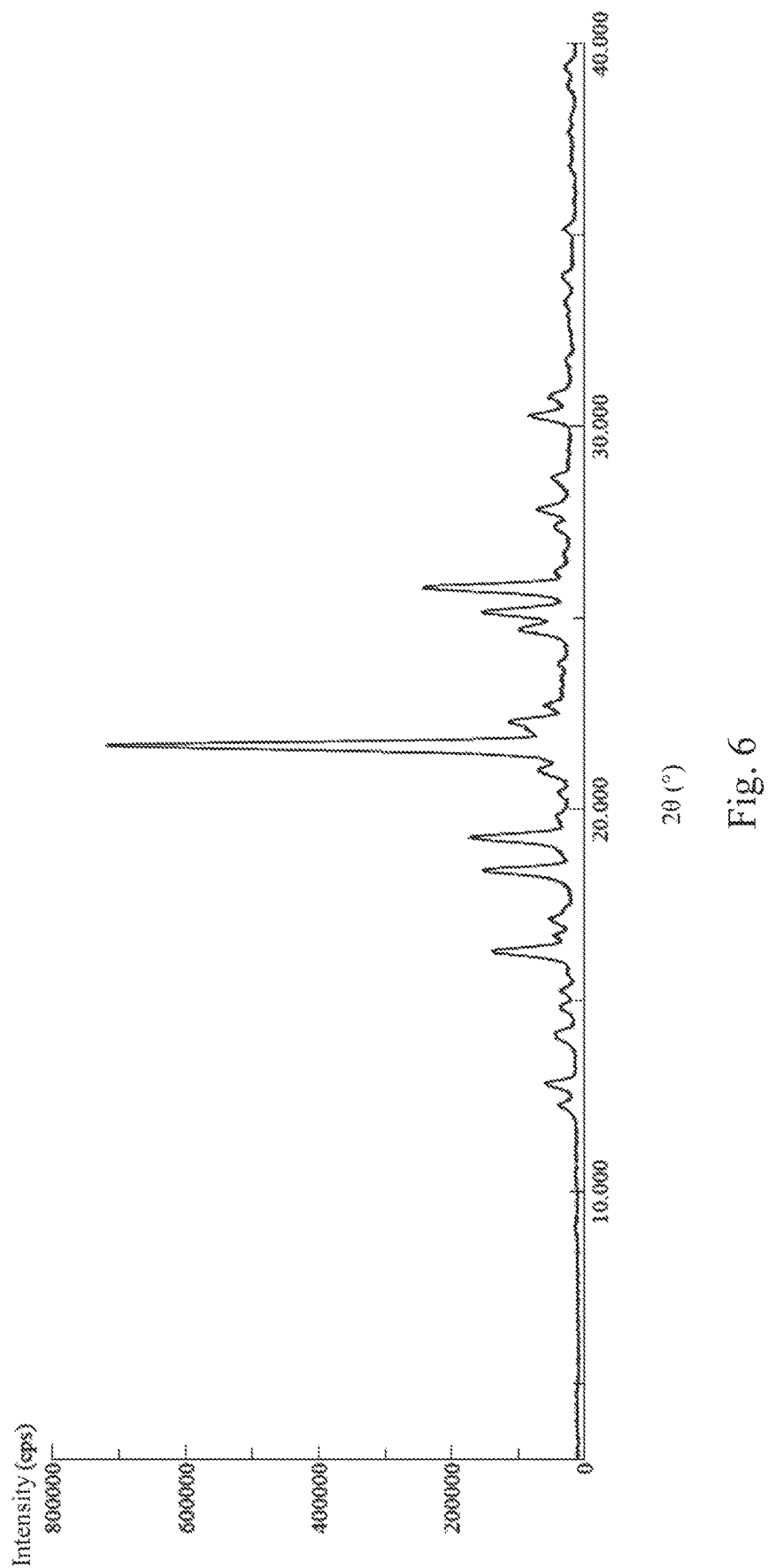
FIG. 6 shows an XRD pattern of the crystal of the compound represented by Formula I.

| No. | Solvent | XRD pattern |
| --- | --- | --- |
| Method III | acetonitrile | FIG. 5 |
| Method IV | ethanol | FIG. 6 |

In Example 3, the crystals of the compound represented by Formula I obtained by using different crystallization solvents all belong to the same crystalline form.

Example 4: A Crystal of the Phosphate of (2R,3S,5R)-5-(5-methanesulfonylisoindolin-2-yl)-2-(2,5-difluorophenyl)tetrahydro-2H-pyran-3-amine

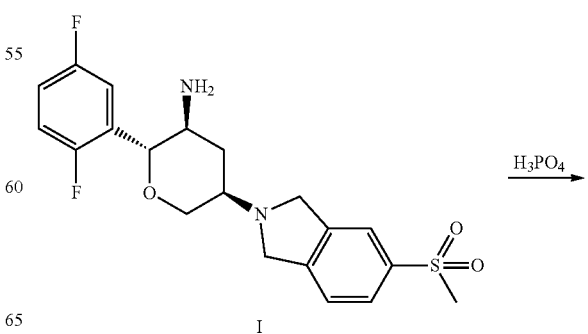

I

-continued

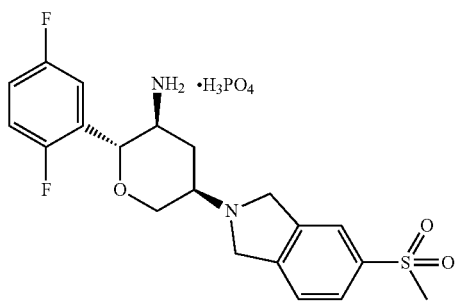

Figure 7:
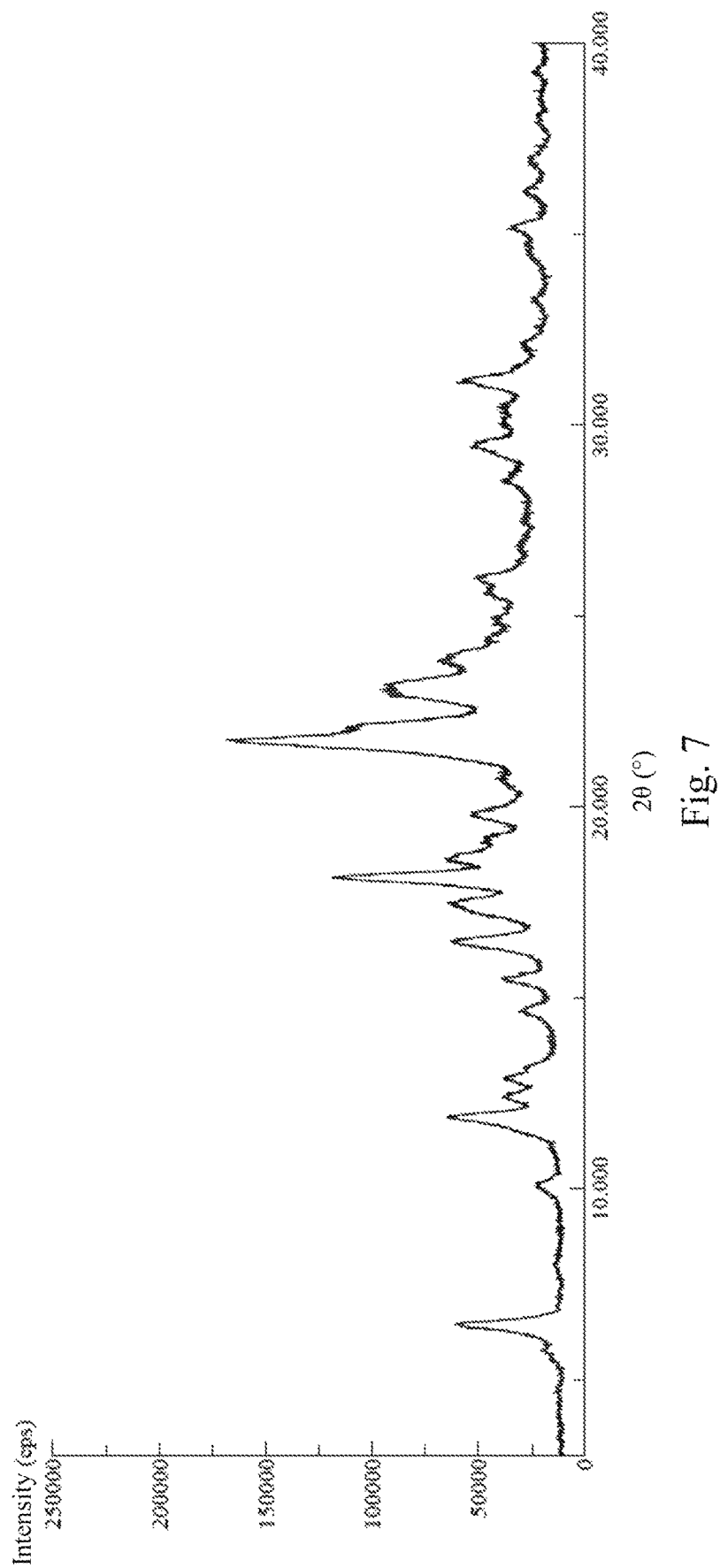
FIG. 7 shows an XRD pattern of the crystal of the phosphate of the compound represented by Formula I.
Figure 8:
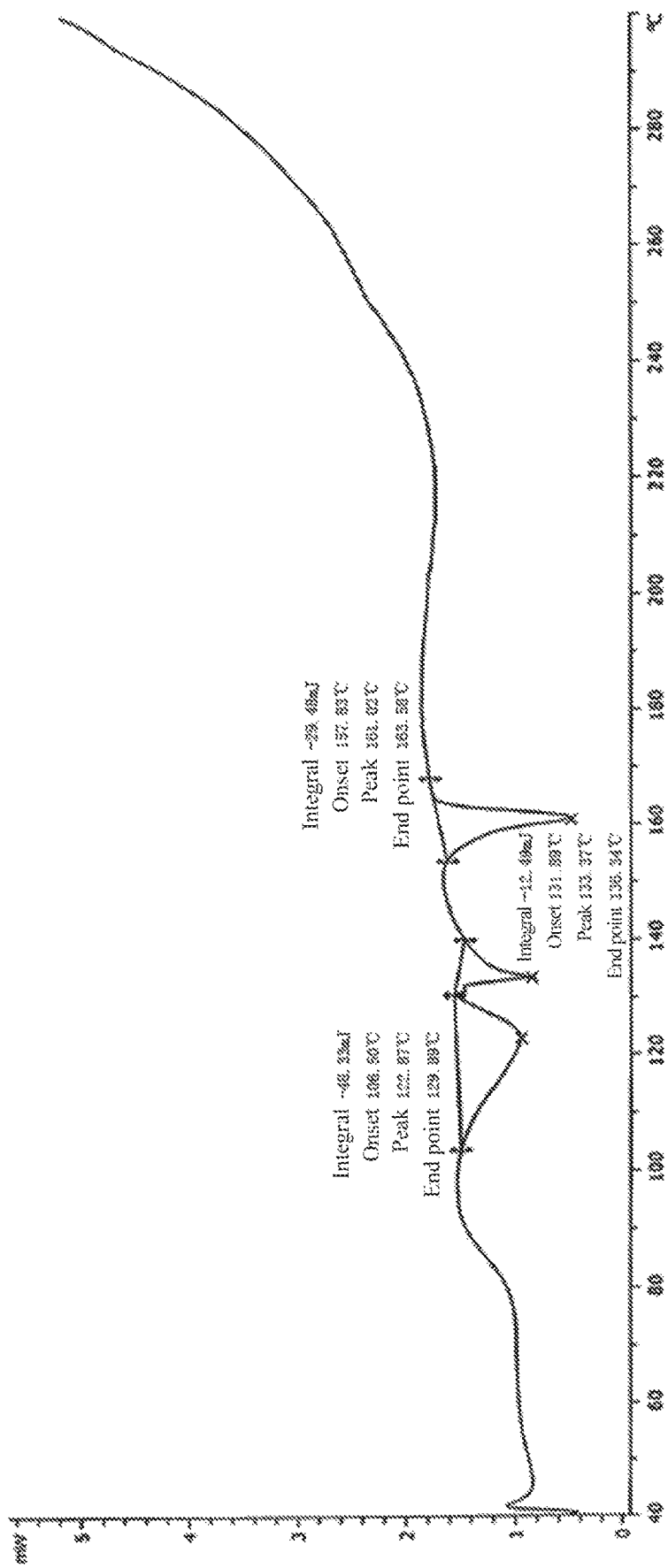
FIG. 8 shows a DSC pattern of the crystal of the phosphate of the compound represented by Formula I.

The compound represented by Formula I (7 g, 17.1 mmol) was added to 350 mL of ethanol solvent, heated to reflux and dissolved to obtain a clear solution. The resulting mixture was then decolorized for 10 min with 1.0 g of activated carbon and hot-filtered under suction. Then to the filtrate was added dropwise a phosphoric acid solution (1.8 mL, 34.2 mmol), and a large amount of white solid was precipitated out. After the dropwise addition was completed, the reaction system was cooled to room temperature and stirred for 2 h, and the solid was continuously precipitated out. The resulting mixture was filtered under suction, and the solid was forced air-dried overnight to afford 8.3 g of a crystal of the phosphate of the compound represented by Formula I (1:1, measured through the titration method). Yield: 95.8%, Purity: 99.12%. The resulting product had a typical XRD pattern as shown in FIG. 7 and a DSC pattern as shown in FIG. 8.

Example 5: A fumarate of (2R,3S,5R)-5-(5-methanesulfonylisoindolin-2-yl)-2-(2,5-difluorophenyl)tetrahydro-2H-pyran-3-amine

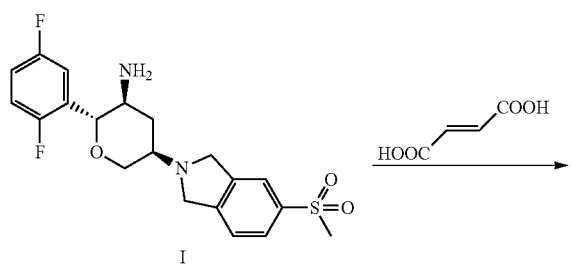

Figure 9:
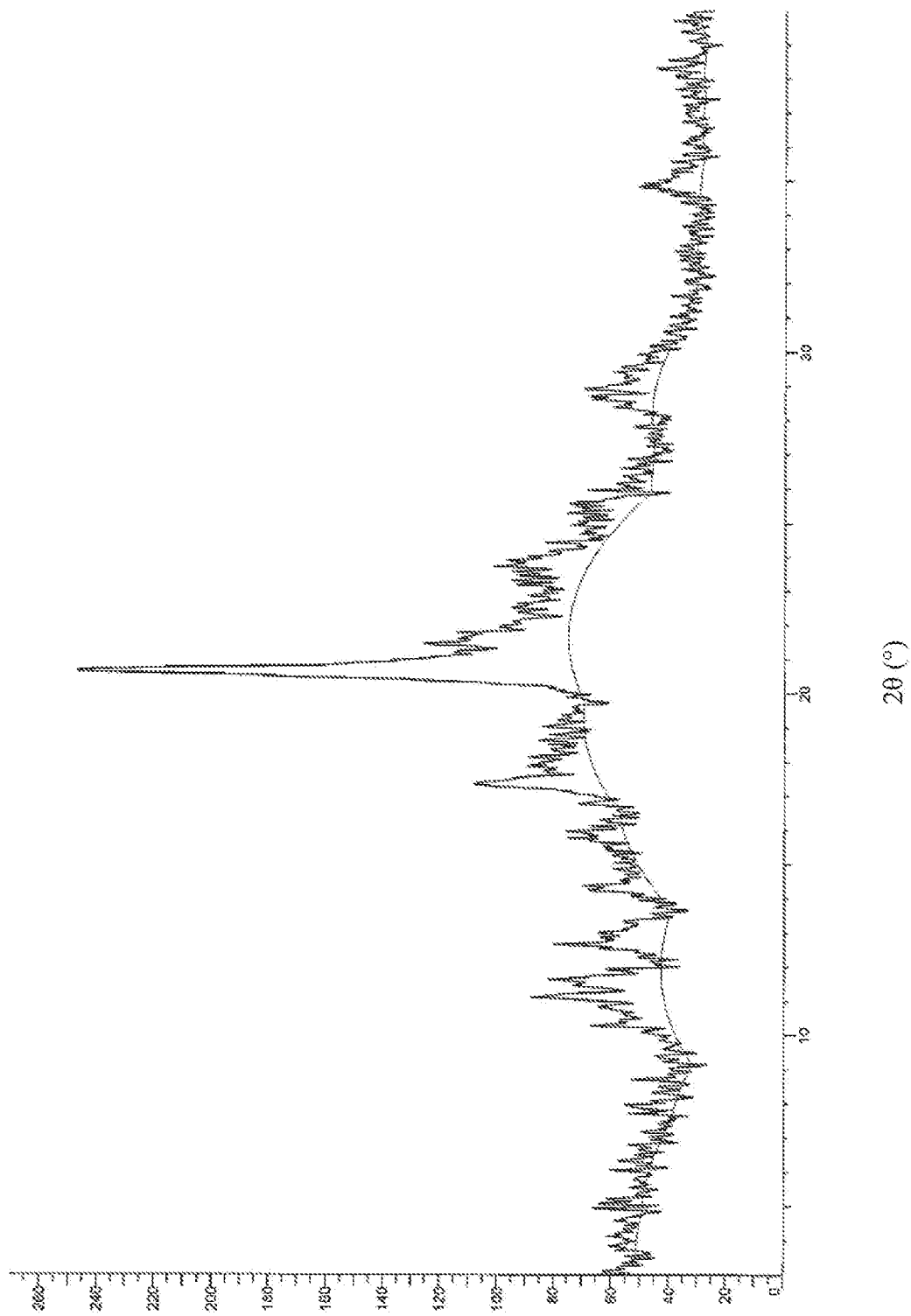
FIG. 9 shows an XRD pattern of the crystal of the fumarate of the compound represented by Formula I.
Figure 10:
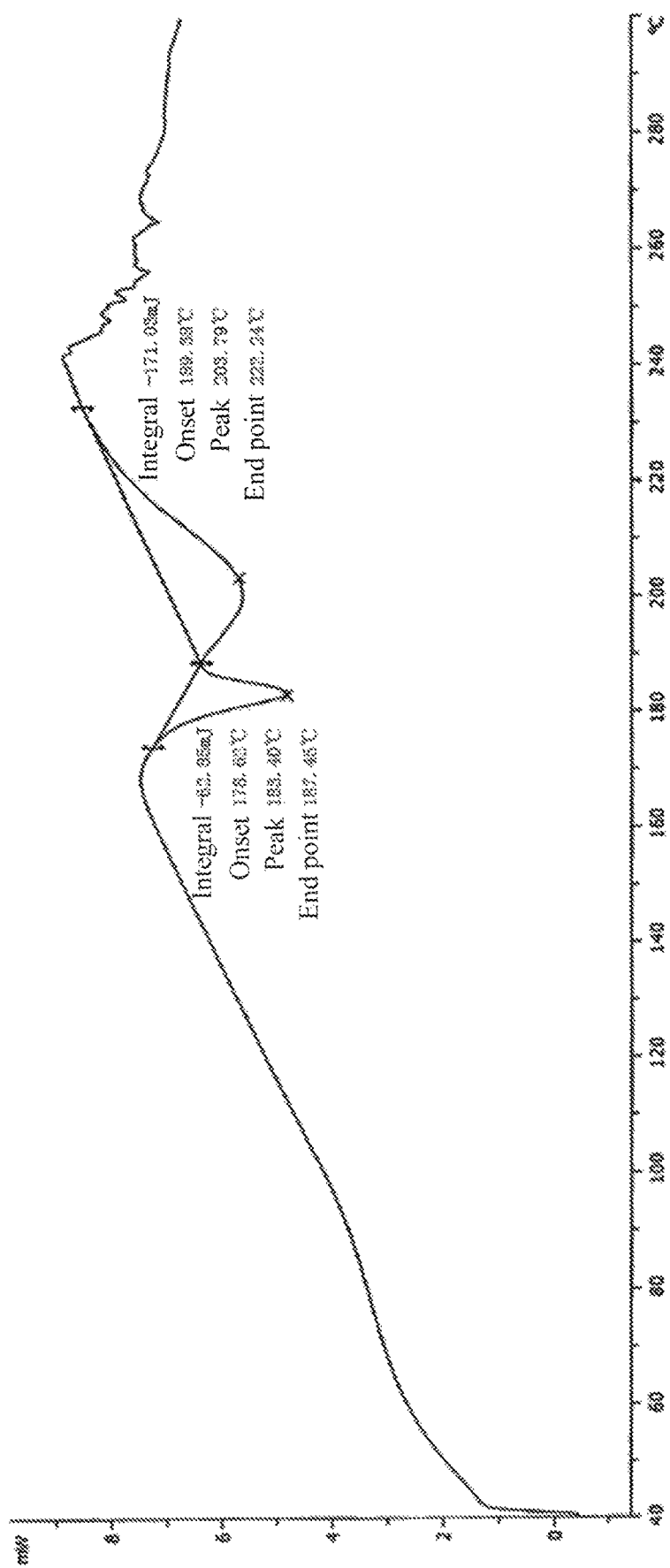
FIG. 10 shows a DSC pattern of the crystal of the fumarate of the compound represented by Formula I.
Figure 11:
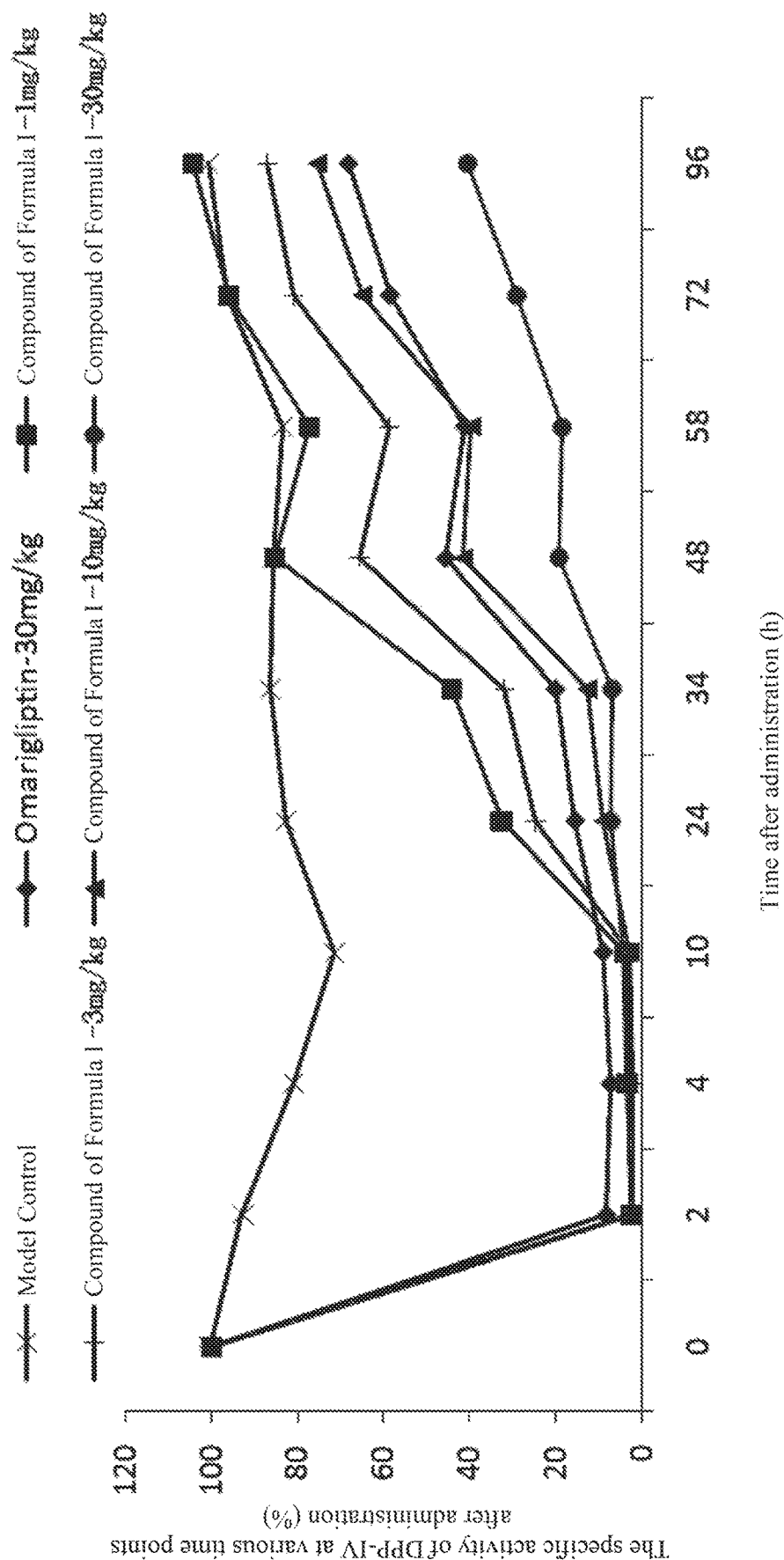
FIG. 11 shows the inhibitory effect of the compound represented by Formula I on serum DPP-IV activity in ob/ob mice.

The compound represented by Formula I (7 g, 17.1 mmol) was added to 350 mL of ethanol solvent, heated to reflux and dissolved to obtain a clear solution. The resulting mixture was then decolorized for 10 min with 1.0 g of activated carbon and hot-filtered under suction. Then to the filtrate was added fumaric acid (3.97 g, 34.2 mmol). After the addition was completed, the reaction system was cooled to room temperature and then stirred for 2 h in an ice water bath, and a solid was precipitated out. The resulting mixture was filtered under suction, and the solid was forced air-dried for 6 h at 50° C. to afford 7.2 g of the fumarate of the compound represented by Formula I (1:0.5, measured through the titration method). Yield: 80.3%, Purity: 97.7%. The resulting product had a typical XRD pattern as shown in FIG. 9 and a DSC pattern as shown in FIG. 10.

Experimental Example 1: Stability Test of the Crystal of the Compound Represented by Formula I The stability of the crystal of the compound represented by Formula I according to the present application at a temperature of 40° C. or 60° C. or under high humidity (RH 92.5%) or light irradiation condition was tested in accordance with "Guidelines for Stability Tests of Active Pharmaceutical Ingredients and Pharmaceutical Preparations" (Chinese Pharmacopoeia, 2010 edition, Appendix XIXC). Samples were taken on day 5 or day 10 and tested, respectively, and the results were compared with the initial results. The test results were shown in Table 1 below.

TABLE 1

Stability test results of the crystal of the compound represented by Formula I

| Item | Day 0 | 40° C. | | 60° C. | | High Humidity (RH92.5%, 25° C.) | | Light Irradiation (6000 lux) | |
| --- | --- | --- | --- | --- | --- | --- | --- | --- | --- |
| | | Day 5 | Day 10 | Day 5 | Day 10 | Day 5 | Day 10 | Day 5 | Day 10 |
| Content (%) | 99.1 | 99.6 | 99.6 | 100.2 | 99.4 | 100.3 | 99.9 | 99.5 | 99.3 |
| Total impurity (%) | 0.39 | 0.31 | 0.37 | 0.30 | 0.33 | 0.27 | 0.32 | 0.33 | 0.44 |
| Appearance | Off-white powdered solid | | | | | | | | |

Experimental Example 2: Pharmacokinetics of the Compound Represented by Formula I and Salts Thereof in Crystalline Form Male Beagle dogs (10±1 kg body weight) were randomly divided into 3 groups (3 dogs per group) after 7 days of adaptation, and administrated the crystal of the compound represented by Formula I, the crystal of the fumarate of the compound represented by Formula I, and the crystal of the phosphate of the compound represented by Formula I at a dosage of 2 mg/kg body weight (in free form), respectively.

Male Beagle dogs were fasted for about 12 h prior to administration and had free access to water. The dogs were also fasted for 4 hours after administration. Blood samples (0.8 mL) were taken from the forelimb vein of the subject Beagle dogs at 0.25, 0.5, 1, 2, 4, 6, 8, 10, 24, 30, 48, and 72 h after administration. The samples were then placed in EDTA-K2 centrifuge tubes, stored at 4° C., and centrifuged for 10 min at a speed of 4000 rpm at 4° C. within 0.5 h after blood collection to separate plasma. The plasma was stored at ~20° C. within 1 h after collecting all the plasma.

300 μL of a solution of an internal standard substance in methanol was added to 50 μL of the plasma sample to be tested and a standard curve sample, respectively. The resulting mixture was mixed uniformly by shaking for 5 min, and centrifuged for 10 min at a speed of 13000 rpm. Then 80 μL of supernatant was taken, and 5 μL of the supernatant was pipetted for LC/MS/MS determination, and the chromatogram was recorded.

The oral bioavailabilities of the compound represented by Formula I according to the present application and the salts thereof were evaluated through in vivo pharmacokinetic experiment in beagle dogs. The pharmacokinetic parameters of the compound represented by Formula I and the salts thereof were shown in the table below.

TABLE 2

Pharmacokinetic experiment results of the compound represented by Formula I and the salts thereof

| PK parameter | The compound represented by Formula I | | The fumarate of the compound represented by Formula I | | The phosphate of the compound represented by Formula I | |
|---|---|---|---|---|---|---|
| | Mean | ±SD | Mean | ±SD | Mean | ±SD |
| $T_{max}$ (h) | 6.00 | 3.46 | 0.75 | 0.35 | 0.67 | 0.29 |
| $C_{max}$ (ng/mL) | 926 | 188 | 1215 | 140 | 1746 | 771 |
| $AUC_{(0-t)}$ (ng*h/mL) | 15150 | 4131.5 | 19527 | 1982 | 22746 | 6216 |
| $AUC_{(0-\infty)}$ (ng*h/mL) | 15768 | 4404.1 | 20303 | 1908 | 23508 | 6100 |
| $MRT_{(0-t)}$ (h) | 20.6 | 3.07 | 20.3 | 1.18 | 17.9 | 3.49 |
| $t_{1/2}$(h) | 16.4 | 0.63 | 16.6 | 1.15 | 16.9 | 2.57 |
| $AUC_{(0-t)}$/Does | 6101 | 1224 | 9260 | 580 | 10116 | 877 |
| Relative F % | 100% | | 152% | | 166% | |

Experimental Example 3: Determination of Inhibitory Activity Against DPP-IV Enzyme The inhibitory activity of the compound represented by Formula I according to the present application against DPP-IV enzyme in plasma was determined by using the following method. The inhibitory activity was expressed as $IC_{50}$ values, i.e., the concentration of the compound required to achieve 50% inhibition of DPP-IV enzyme activity.

Materials and Methods:

Materials:

a. White 384-well plate (Perkin Elmer, Catalog No. 607290/99)
b. HEPES buffer: using 1M HEPES buffer (Invitrogen, Catalog No. 15630-080) to prepare 50 ml of 0.5M HEPES buffer by following the steps of taking 25 mL of 1 M HEPES buffer, adding an appropriate amount of ddH$_2$O (re-distilled water), adjusting the pH to 7.8 with NaOH, and finally adding ddH$_2$O to 50 mL.
c. Rat plasma: taking blood samples from rat orbit, adding heparin for anticoagulation, centrifuging for 10 minutes at 4000 rpm, taking supernatant plasma as an enzyme source of DPP-IV.
d. H-Gly-Pro-AMC (glycine-proline-7-amino-4-methylcoumarin) as the enzyme reaction substrate of DPP-IV, which was synthesized by one of the applicants, was dissolved in DMSO to form 100 mM mother solution.
e. 1M MgCl$_2$
f. 1.5M NaCl
g. 10% BAS
h. DMSO (dimethylsulphoxide)
i. ddH$_2$O
j. Test compounds: Omarigliptin as a positive control compound and the compound represented by Formula I of the present application.

Following the Sequence Below:

1. DPP-IV enzyme reaction buffer was prepared (50 mM HEPES (pH=7.8), 80 mM MgCl$_2$, 150 mM NaCl, 1% BSA), and stored on ice for use:
2. The test compounds were diluted with DMSO from 10 mM to 1 mM (100-fold final working concentration), and then diluted gradiently 3 folds in a 96-well plate to obtain 11 concentrations; DMSO was added to the twelfth well as a blank control, and then diluted 25 folds with the enzyme reaction buffer to 4-fold final working concentration for use;
3. The DPP-IV enzyme reaction substrate H-Gly-Pro-AMC was thawed and diluted to 160 μM (4-fold working concentration) with the enzyme reaction buffer, and then stored on ice for use:
4. The rat plasma was thawed and diluted 100 folds (2-fold working concentration) with the enzyme reaction buffer, and then stored on ice for use;
5. 5 μL of the test compounds (4-fold concentration) were added to a 384-well plate, and then 10 μL of the rat plasma (2-fold working concentration) was added, centrifuged and mixed well:
6. 5 μL of the enzyme reaction substrate H-Gly-Pro-AMC (4-fold working concentration) was added, centrifuged and mixed well, and then the 384-well plate was sealed with a film:
7. The resulting mixture was incubated in an incubator (22-23° C.) for 1 hour:
8. The fluorescence signal was determined using FlexStation13 (Molecular devices) microplate reader (excited at 380 nm, and the emission spectrum was determined at 460 nm wavelength);
9. $IC_{50}$ values of the test compounds in inhibiting DPP-IV enzyme activity were determined, i.e., calculating the $IC_{50}$ values of the compounds using GraFit6 software.

TABLE 3

Inhibitory activity of the compound represented by Formula I against DPP-IV enzyme

| Compound | Structure | $IC_{50}$ (nM) |
|---|---|---|
| Omarigliptin | *(structure)* | 4.2 |
| The compound represented by Formula I | *(structure)* | 2.6 |

Experimental Example 4: Determination of $IC_{50}$ Value of Inhibiting CYP Enzyme System $IC_{50}$ value of the compound represented by Formula I of the present application in inhibiting CYP enzyme system was determined by using the following method.

Human liver microsomes frozen at −80° C. were placed on ice for thawing, of which 100 μL was placed in a constant temperature oscillator for incubation (1 hour) at 60° C. and 100 rpm when immediately thawing, and the rest was frozen immediately at −80° C. After one hour, 100 μL inactivated liver microsomes were taken out, and thereto was added 400 μL phosphate buffer, and uniformly mixed to form a 4 mg/mL solution of inactivated liver microsomes. Meanwhile, human liver microsomes frozen at −80° C. were placed on ice for thawing, of which 100 μL was taken out when immediately thawing, and thereto was added 400 μL phosphate buffer, and uniformly mixed to form a 4 mg/mL solution of liver microsomes. The incubation mixtures for a positive control, test compounds and a negative control were prepared according to Table 4 below:

TABLE 4

Incubation mixtures for a positive control, test compounds and a negative control

| CYP450 Enzyme | Positive Control and Test Compounds | | | Negative Control | | |
|---|---|---|---|---|---|---|
| | Liver Microsoms Solution (μL) | Substrate Solution (μL) | Phosphate Buffer (μL) | Inactivated Liver Microsomes Solution (μL) | Substrate Solution (μL) | Phosphate Buffer (μL) |
| CYP1A2 | 13.0 | 88.0 | 3109.0 | 6.5 | 44.0 | 1554.5 |
| CYP2B6 | 7.0 | 88.0 | 3115.0 | 3.5 | 44.0 | 1557.5 |
| CYP2C8 | 30.0 | 88.0 | 3126.0 | 15.0 | 44.0 | 1563.0 |
| CYP2C9 | 35.0 | 88.0 | 3121.0 | 17.5 | 44.0 | 1560.5 |
| CYP2C19 | 175 | 88.0 | 2960.0 | 87.5 | 44.0 | 1480.0 |
| CYP2D6 | 13.0 | 116.0 | 3073.0 | 6.5 | 58.0 | 1536.5 |
| CYP3A4 Midazolam | 20.0 | 88.0 | 3078.0 | 10.0 | 44.0 | 1539.0 |
| CYP3A4 Testosterone | 23.0 | 90.0 | 3151.6 | 11.5 | 45.0 | 1575.8 |

The above incubation mixtures were incubated for 5 minutes in a constant temperature oscillator at 37° C. and 100 rpm.

To 2.5 μL working solution of the test compounds or positive control (the negative control was added to the working solution of the test compounds) were added 91.5 μL the incubation mixtures and 6 μL NADPH solution, and then the reaction was initiated via vortex. The resulting solutions were incubated in a constant temperature oscillator at 37° C. and 100 rpm, and the incubation time was shown in Table 5 below:

TABLE 5

Incubation Time

| CYP450 Enzyme | CYP 1A2 | CYP 2B6 | CYP 2C8 | CYP 2C9 | CYP 2C19 | CYP 2D6 | CYP3A4 Midazolam | CYP3A4 Testosterone |
|---|---|---|---|---|---|---|---|---|
| Time (min) | 30 | 20 | 15 | 15 | 30 | 30 | 10 | 20 |

After incubation, 200 μL of an internal standard solution (the internal standard solution of CYP2C19 was a 100 ng/mL solution of chloramphenicol in acetonitrile, and other internal standard solutions were a 250 ng/mL solution of warfarin in acetonitrile and 500 ng/mL solution of propranolol in acetonitrile) was added to terminate the reaction. Samples from the terminated reaction were centrifuged at 12000 rpm for 10 minutes, and supernatants were taken out for analysis.

Analyst 1.4.2 or equivalent software was used for data processing. Integrals were detected to ensure that all peaks were properly integrated, and if necessary, adjust integral parameters.

The quantification of an analyte was defined as a ratio of a peak area of the analyte to that of the internal standard. LC-MS/MS method was used for analysis. Parameters, such as $IC_{50}$ and the like, were calculated using the Graphpad Prism (Version 5.03) software. The results were shown in Table 6 below:

TABLE 6

$IC_{50}$ (μM) of the compound represented by Formula I in inhibiting CYP Enzyme System

| CYP Enzyme System | 1A2 | 2B6 | 2C8 | 2C9 | 2C19 | 2D6 | 3A4_Mid | 3A4_Tes |
|---|---|---|---|---|---|---|---|---|
| Positive Control | α-Naphthoflavone | Ticlopidine | Quercetin | Sulfaphenzole | Ticlopidine | Quinidine | Ketoconazole | Ketoconazole |
| Compound represented by Formula I | >25 | >25 | >25 | >25 | >25 | >25 | >25 | >25 |
| Positive Control | 0.025 | 0.10 | 1.13 | 0.44 | 1.71 | 0.11 | 0.054 | 0.033 |

Experimental Example 5: Liver Microsome Metabolic Stability

The liver microsome metabolic stability of the compound represented by Formula I was determined by using the following method.

8 μL human liver microsomes (20 mg/mL), 20 μL NADPH and 368 μL of 0.1 M phosphate buffer were mixed, and then pre-incubated at 37° C. for 5 minutes. 4 μL working solutions (test compounds or positive control) were added, respectively. When pre-incubated at 37° C., 50 μL incubation solutions were taken out at 0, 10, 20, 30, 45 and 60 minute, and thereto was added a 150 μL solution of internal standard (0.25M warfarin) in acetonitrile. 4 μL rat liver microsomes (20 mg/mL), 10 μL NADPH and 184 μL of 0.1 M phosphate buffer were mixed, and then pre-incubated at 37° C. for 5 minutes. 2 μL working solutions (test compounds or positive control) were added, respectively. When pre-incubated at 37° C., 20 μL incubation solutions were taken out at 0, 10, 20, 30, 45 and 60 minute, and thereto was added a 180 μL solution of internal standard (0.25 M warfarin) in acetonitrile. All samples were vortexed and centrifuged at 4000 rpm for 15 min, and 150 μL supernatants were added to a 96-well plate, and then 5 μL supernatants were detected in LC/MS/MS system. Chromatographic column for analysis was C18 1.7 μm 2.1×50 mm (Waters). Triple quadrupole mass spectrometry (API4000, AB Company) was used in detection. A ratio of the peak area of CT-1225 to that of the internal standard was detected in positive ion mode. A half-life was represented as a ratio of the peak area of test compounds/internal standard to time. The results were shown in Table 7 below:

TABLE 7

Liver microsome metabolic stability of the compound represented by Formula I and reference compound

| Compound | Half Life $t_{1/2}$ (hour) | |
|---|---|---|
| | Rat | Human |
| Compound represented by Formula I | 8.26 | 4.52 |
| Omarigliptin | 21.1 | 4.09 |

Experimental Example 6: Inhibitory Effect of a Single Dose on Serum DPP-IV Activity in Ob/Ob Mice 36 female ob/ob mice were randomly divided into 6 groups (6 mice in each group), which are model control group, 1 mg/kg of the compound represented by Formula I group, 3 mg/kg of the compound represented by Formula I group, 10 mg/kg of the compound represented by Formula I group, 30 mg/kg of the compound represented by Formula I group and 30 mg/kg of Omarigliptin (as positive control) group. The mice were orally administered with the compound represented by Formula I or Omarigliptin at various doses, except that the mice in model control group were orally administered with 0.25% CMC-Na Blood samples were taken before administration and at 2, 4, 10, 24, 34, 48, 58, 72 and 96 h after administration, and the serum was separated to determine serum DPP-IV activity.

Method for determining the serum DPP-IV activity: to 5 μL serum sample was added 45 μL of 80 mM $MgCl_2$ buffer, mixed well, and pre-incubated at room temperature for 5 minutes; thereto were added 10 μL of 0.1 mM the reaction substrate Gly-Pro-7-AMC and 40 μL buffer, and kept away from light; after mixing well, fluorescence determination was performed (excitation wave 380 nm/emission wave 460 nm) every 3 minutes for 18 minutes with a total of 6 times; time-fluorescence curve was made based on the determination results minus the blank background, in which the slope was activity value; the serum DPP-IV activity at 0 h before administration was settled as 100%; and a specific activity at each time point after administration was calculated according to the following formula: specific activity (%)=activity after administration/activity before administration×100%.

Experimental results: after ob/ob mice were orally administered once with the compound represented by Formula I at various doses, the serum DPP-IV activity was significantly inhibited in dose- and time-dependent manner. The inhibitory rate of serum DPP-IV activity in mice was higher than 70% over 10 hours after the administration of 1 mg/kg of the compound represented by Formula I. The inhibitory rate of serum DPP-IV activity in mice was higher than 70% over 24 hours after the administration of 3 mg/kg of the compound represented by Formula I. The inhibitory rate of the serum DPP-IV activity in mice was higher than 70% over 34 hours after the administration of 10 mg/kg of the compound represented by Formula I. The inhibitory rate of serum DPP-IV activity in mice was higher than 70% over 72 hours after the administration of 30 mg/kg of the compound represented by Formula I. The inhibitory rate of the serum DPP-IV activity in mice in the 30 mg/kg of Omarigliptin (as the positive control) group was higher than 70% over 34 hours after administration.

TABLE 8

Inhibition results of the compound represented by Formula I and reference compounds on serum DPP-IV activity in mice

| Group | Dose (mg/kg) | Specific activity of DPP-IV at various time points after administration (%) | | | | | | | | | |
|---|---|---|---|---|---|---|---|---|---|---|---|
| | | 0 h | 2 h | 4 h | 10 h | 24 h | 34 h | 48 h | 58 h | 72 h | 96 h |
| Model Control | — | 100 | 92.6 | 80.7 | 71.3 | 82.7 | 86.2 | 85.6 | 83.4 | 96.2 | 100.4 |
| Omarigliptin | 30 | 100 | 8.4 | 7.4 | 9.1 | 15.6 | 20.2 | 45.5 | 41.2 | 58.4 | 68.0 |
| Compound represented by Formula I | 1 | 100 | 2.5 | 3.4 | 4.0 | 32.6 | 44.0 | 85.3 | 77.3 | 95.9 | 104.3 |
| | 3 | 100 | 2.4 | 2.3 | 3.0 | 24.9 | 32.2 | 65.4 | 58.7 | 80.7 | 87.0 |
| | 10 | 100 | 2.2 | 3.2 | 3.1 | 9.0 | 12.8 | 41.3 | 39.5 | 64.8 | 75.3 |
| | 30 | 100 | 2.3 | 3.9 | 4.4 | 7.3 | 6.9 | 19.2 | 18.6 | 29.3 | 40.4 |

What is claimed is:

1. A crystal of a compound represented by Formula I,

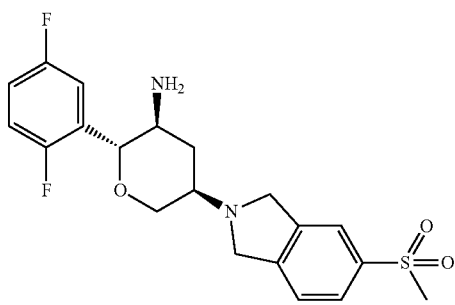 [SMILES: CS(=O)(=O)c1ccc2c(c1)CN([C@H]1CO[C@H](c3cc(F)ccc3F)[C@@H](N)C1)C2]

I comprising X-ray diffraction peaks at 2θ values 16.4°, 21.8°, 25.3°, and 26.0°±0.2° in an X-ray diffraction pattern.

2. The crystal of claim 1, wherein an onset temperature is 193.3±5° C. and a peak temperature is 195.2±5° C. when characterized by DSC.

3. The crystal of claim 1, wherein the X-ray diffraction peaks are characterized by the following characteristics:

| No. | 2θ ± 0.2 (°) | Relative Intensity (%) |
|---|---|---|
| 1 | 12.3 | 3 |
| 2 | 13.0 | 8 |
| 3 | 15.0 | 5 |
| 4 | 16.4 | 18 |
| 5 | 17.2 | 5 |
| 6 | 17.6 | 3 |
| 7 | 18.5 | 9 |
| 8 | 19.4 | 12 |
| 9 | 21.2 | 16 |
| 10 | 21.8 | 100 |
| 11 | 22.1 | 9 |
| 12 | 22.5 | 11 |
| 13 | 22.8 | 5 |
| 14 | 24.8 | 7 |
| 15 | 25.3 | 17 |
| 16 | 26.0 | 39 |
| 17 | 26.4 | 4 |
| 18 | 27.5 | 4 |
| 19 | 27.9 | 6 |
| 20 | 28.8 | 4 |
| 21 | 30.4 | 7 |
| 22 | 30.9 | 4 |
| 23 | 32.0 | 6 |
| — | — | —. |

4. A crystalline composition, comprising the crystal of claim 1 which accounts for 50% or more by weight of the crystalline composition.

5. A crystal of a salt wherein the structure is:

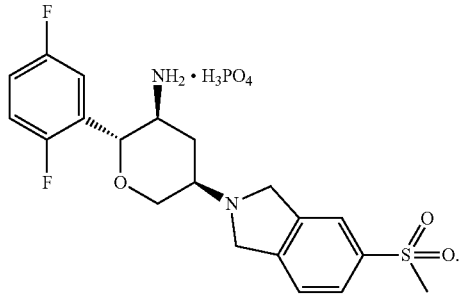

comprising diffraction peaks at 2θ values of 6.4°, 11.9°, 18.2°, 21.7°, 22.1°, 22.9°, and 23.2°±0.2° in an X-ray diffraction pattern.

6. A crystalline composition, comprising the crystal of claim 5 which accounts for 50% or more by weight of the crystalline composition.

7. A crystal of a salt wherein the structure is:

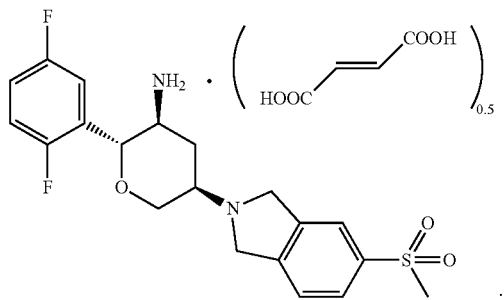

characterized by the X-ray powder diffraction pattern of FIG. 9.

8. A crystalline composition, comprising the crystal of claim 7 which accounts for 50% or more by weight of the crystalline composition.

9. A pharmaceutical composition, comprising a therapeutically effective amount of the crystal of claim 1.

10. A method for the treatment of type II diabetes in a subject in need thereof, comprising administering to the subject the crystal of claim 1.

11. A method for the treatment of type II diabetes in a subject in need thereof, comprising administering to the subject the crystal of claim 5.

12. A method for the treatment of type II diabetes in a subject in need thereof, comprising administering to the subject the crystal of claim 7.

13. The crystal of claim 1, comprising diffraction peaks at 2θ values of 16.4°, 19.4°, 21.2°, 21.8°, 25.3°, and 26.0°±0.2° in the X-ray diffraction pattern.

14. The crystal of claim 1, comprising diffraction peaks at 2θ values of 13.0°, 16.4°, 18.5°, 19.4°, 21.2°, 21.8°, 25.3°, and 26.0°±0.2° in the X-ray diffraction pattern.

15. The crystal of claim 5, comprising diffraction peaks at 2θ values of 6.4°, 11.9°, 16.5°, 17.5°, 18.2°, 18.6°, 21.7°, 22.1°, 22.9°, and 23.2°±0.2° in the X-ray diffraction pattern.

16. The crystal of claim 5, comprising diffraction peaks at 2θ values of 6.4°, 10.1°, 11.9°, 16.5°, 17.5°, 18.2°, 18.6°, 19.8°, 21.7°, 22.1°, 22.9°, 23.2°, and 23.8°±0.2° in the X-ray diffraction pattern.

17. A crystalline composition, comprising the crystal of claim 1 which accounts for 80% or more by weight of the crystalline composition.

18. A crystalline composition, comprising the crystal of claim 5 which accounts for 80% or more by weight of the crystalline composition.

\* \* \* \* \*

UNITED STATES PATENT AND TRADEMARK OFFICE
CERTIFICATE OF CORRECTION

PATENT NO. : 10,822,319 B2
APPLICATION NO. : 16/324884
DATED : November 3, 2020
INVENTOR(S) : Guangming Sang et al.

Page 1 of 1

It is certified that error appears in the above-identified patent and that said Letters Patent is hereby corrected as shown below:

On the Title Page

In Column 2, item (56), (Other Publications), Line 2, Delete "334.*" and insert -- 334).* --, therefor.

In the Claims

In Column 25, Line 65, in Claim 1, After "values" insert -- of --.

In Column 26, Lines 54-67, in Claim 5, Delete

" 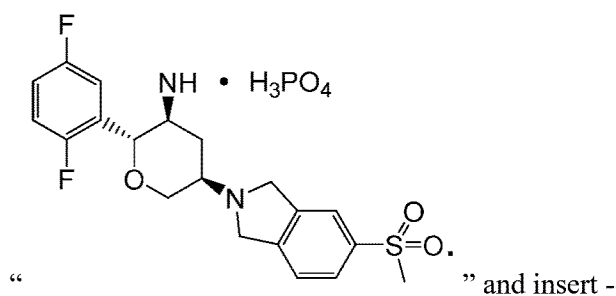 " and insert -- 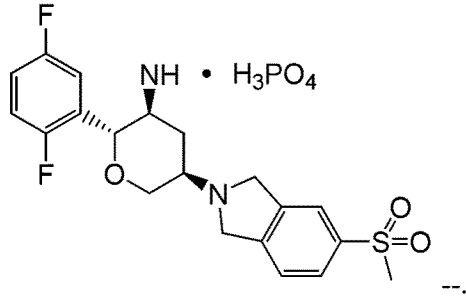 --.

In Column 27, Lines 10-21, in Claim 7, Delete

" 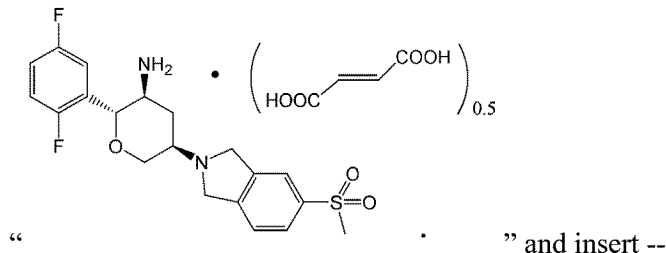 " and insert -- 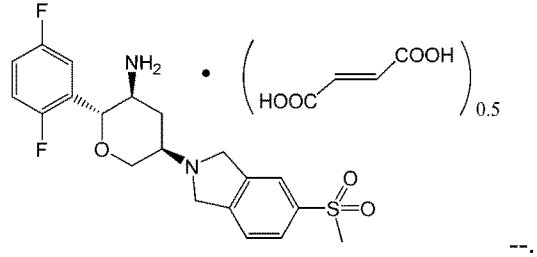 --.

Signed and Sealed this
Ninth Day of February, 2021

Drew Hirshfeld
*Performing the Functions and Duties of the
Under Secretary of Commerce for Intellectual Property and
Director of the United States Patent and Trademark Office*